United States Patent
Yalin et al.

(10) Patent No.: US 7,420,662 B2
(45) Date of Patent: Sep. 2, 2008

(54) OPTICAL DIAGNOSTICS INTEGRATED WITH LASER SPARK DELIVERY SYSTEM

(75) Inventors: Azer Yalin, Fort Collins, CO (US);
Bryan Willson, Fort Collins, CO (US);
Morgan Defoort, Fort Collins, CO (US);
Sachin Joshi, Fort Collins, CO (US);
Adam Reynolds, Fort Collins, CO (US)

(73) Assignee: Colorado State University Research Foundation, Fort Collins, CO (US)

( * ) Notice: Subject to any disclaimer, the term of this patent is extended or adjusted under 35 U.S.C. 154(b) by 195 days.

(21) Appl. No.: 11/197,833

(22) Filed: Aug. 4, 2005

(65) Prior Publication Data
US 2006/0037572 A1 Feb. 23, 2006

Related U.S. Application Data

(63) Continuation-in-part of application No. 11/126,908, filed on May 10, 2005.

(60) Provisional application No. 60/598,932, filed on Aug. 4, 2004.

(51) Int. Cl.
*G01J 3/30* (2006.01)
(52) U.S. Cl. .......................... 356/72; 356/317
(58) Field of Classification Search ................ 356/72, 356/318
See application file for complete search history.

(56) References Cited

U.S. PATENT DOCUMENTS

| 3,258,910 | A | | 7/1966 | Seymour |
|---|---|---|---|---|
| 4,314,530 | A | | 2/1982 | Giacchetti |
| 4,416,226 | A | | 11/1983 | Nishida et al. |
| 4,523,552 | A | | 6/1985 | Mukainakano et al. |
| 4,852,529 | A | | 8/1989 | Vowles |
| 4,917,014 | A | * | 4/1990 | Loughry et al. ............ 102/201 |
| 5,328,665 | A | | 7/1994 | Geiger |

(Continued)

FOREIGN PATENT DOCUMENTS

| JP | 63-90643 | | 4/1988 |
|---|---|---|---|
| JP | 63-105261 | | 5/1988 |
| WO | WO 98/11388 | * | 3/1998 |

OTHER PUBLICATIONS

Lee et al.; "Laser Spark Ignition of Chemically Reactive Gases"; *AIAA Journal*; 1969, 7(2):312-317.

(Continued)

*Primary Examiner*—F. L Evans
(74) *Attorney, Agent, or Firm*—Sheridan Ross P.C.

(57) ABSTRACT

A spark delivery system for generating a spark using a laser beam is provided, and includes a laser light source and a laser delivery assembly. The laser delivery assembly includes a hollow fiber and a launch assembly comprising launch focusing optics to input the laser beam in the hollow fiber. The laser delivery assembly further includes exit focusing optics that demagnify an exit beam of laser light from the hollow fiber, thereby increasing the intensity of the laser beam and creating a spark. Other embodiments use a fiber laser to generate a spark. Embodiments of the present invention may be used to create a spark in an engine. Yet other embodiments include collecting light from the spark or a flame resulting from the spark and conveying the light for diagnostics. Methods of using the spark delivery systems and diagnostic systems are provided.

51 Claims, 14 Drawing Sheets

U.S. PATENT DOCUMENTS

| | | | |
|---|---|---|---|
| 5,367,869 A | 11/1994 | DeFreitas | |
| 5,617,717 A | 4/1997 | Asquith et al. | |
| 5,673,550 A | 10/1997 | Few et al. | |
| 5,983,871 A | 11/1999 | Gordon et al. | |
| 6,053,140 A | 4/2000 | Feichtinger et al. | |
| 6,520,142 B2 | 2/2003 | Nogi et al. | |
| 6,676,402 B1 | 1/2004 | Early et al. | |
| 6,700,662 B2 | 3/2004 | Gupta et al. | |
| 6,749,726 B2 | 6/2004 | Edelman et al. | |
| 6,762,835 B2 | 7/2004 | Zhang et al. | |
| 6,796,278 B2 | 9/2004 | Ryan, III | |
| 6,802,290 B1 | 10/2004 | Wintner et al. | |
| 6,898,359 B2 | 5/2005 | Soljacic et al. | |
| 6,903,357 B2 | 6/2005 | Robb | |
| 7,114,858 B2 * | 10/2006 | Gupta et al. | 385/88 |
| 2003/0136366 A1 | 7/2003 | Herdin et al. | |
| 2005/0063646 A1 | 3/2005 | Gupta et al. | |
| 2006/0032471 A1 | 2/2006 | Yalin et al. | |
| 2006/0055925 A1 | 3/2006 | Yalin et al. | |

OTHER PUBLICATIONS

Ronney; "Laser Versus Conventional Ignition of Flames"; *Opt. Eng.*; Feb. 1994; 33(2):510-521.

Spiglanin et al.; "Tiime-Resolved Imaging of Flame Kernels: Laser Spark Ignition of $H_2/O_2/Ar$ Mixtures"; *Combustion and Flame*; 1995; 102:310-328.

Ma et al.; "Nd: YAG Laser Ignition of Natural Gas"; *ASME: ICE-Spring Technical Conference, Paper No. 98-ICE-114*; 1998, 30-3:117-125.

Phuoc et al.; "Laser-Induced Spark Ignition of $CH_4$/Air Mixtures"; *Combustion and Flame*; 1999; 119:203-216.

Phuoc; "Brief Communication—Single-Point Versus Multi-Point Laser Ignition: Experimental Measurements of Combustion Times and Pressures"; *Combustion and Flame*; 2000; 122:508-510.

Chen et al.; "Visualization of Laser-Induced Breakdown and Ignition"; *Opt. Exp.*; 2001; 9(7):360-372.

Kopecek et al.; "Laser Ignition of Methane-Air Mixtures at High Pressures"; *Exptl. Therm. and Fluid Sci.*; 2003; 27:499-503.

Beduneau et al.; "Measurements of Minimum Ignition Energy in Premixed Laminar Methane/Air Flow by Using Laser Induced Spark"; *Combustion and Flame*; 2003; 132:653-665.

Lackner et al.; "Investigation of the Early Stages in Laser-Induced Ignition by Schlieren Photography and Laser-Induced Fluorescence Spectroscopy"; *Opt. Exp.*, 2004; 12(19):4546-4557.

Bradley et al.; "Fundamentals of High-Energy Spark Ignition with Lasers"; *Combustion and Flame*; 2004; 138:55-77.

Kopecek et al.; "Laser Ignition of Methane-Air Mixtures at High Pressures and Diagnostics"; *Jnl. Of Eng. for Gas Turb. and Power*; 2005; 127:213-219.

Weinrotter et al.; "Laser Ignition of Ultra-Lean Methane/Hydrogen/Air Mixtures at High Temperature and Pressure"; *Exptl. Therm. and Fluid Sci.*; 2005; 29:569-577.

Ma et al.; "Laser Spark Ignition and Combustion Characteristics of Methane-Air Mixtures"; *Combustion and Flame*; 1998; 112:492-506.

Klett et al.; "Ignition Characteristics of Methane-Air Mixtures Established Using a Rapid Compression Machine"; *ASRE Meeting*; Mar. 15-16, 2005; pp. 1-28.

Dale et al.; "Application of High Energy Ignition Systems to Engines"; *Prog. Energy Comb. Sci.*; 1997; 23:379-398.

Phuoc; "An Experimental and Numerical Study of Laser-Induced Spark in Air"; *Opt. and Lasers in Eng.*; 2005; 43:113-129.

Kandala et al.; "Computational Modeling of Localized Laser Energy Deposition in Quiescent Air"; *AIAA 2002-2160*; 2002; pp. 1-8.

Dors et al.; "Computational Fluid-Dynamic Model of Laser-Induced Breakdown in Air"; *Appl. Optics*; 2003; 42(30):5978-5985.

Rosen et al.; "Laser-Induced Breakdown in Nitrogen and The Rare Gases at 0.53 and 0.35 µm"; *J. Phys. D: Appl. Phys.*; 1987; 20:1264-1276.

Turcu et al.; "Measurement of KrF Laser Breakdown Threshold in Gases"; *Opt. Comm.*; 1997; 134:66-68.

Stakhiv et al.; "Laser Ignition of Engines via Optical Fibers?"; *Laser Physics*; 2004; 14(5):738-747.

Siegman; "Output Beam Propagation and Beam Quality From a Multimode Stable-Cavity Laser"; *IEEE J. Quant. Elect.*; 1993; 29(4):1212-1217.

Adelgren et al.; "Energy Deposition in Supersonic Flows"; *AIAA, Paper 2001-0885*; Jan. 2001.

Kono et al.; "Mechanism of Flame Kernel Formation Produced by Short Duration Sparks"; *Proceedings of the Combustion Institute*; 1989; pp. 1643-1649.

Morsy et al.; "Numerical Simulation of Front Lobe Formation in Laser-Induced Spark Ignition of $CH_4$/Air Mixtures"; *Proceedings of the Combustion Institute*; 2002; 29:1613-1619.

Bradley et al.; "The Measurement of Laminar Burning Velocities and Markstein Numbers for Iso-octane-Air and Iso-octane-n-Heptane-Air Mixtures at Elevated Temperatures and Pressures in an Explosion Bomb"; *Combustion and Flame*; 1998; 115:126-144.

Bradley et al.; "Spark Ignition and the Early Stages of Turbulent Flame Propagation"; *Combustion and Flame*; 1987; 69:71-93.

Kaminski et al. "Spark Ignition of Turbulent Methane/Air Mixtures Revealed by Time-Resolved Planar Laser-Induced Fluorescence and Direct Numerical Simulations"; *Proceedings of the Combustion Institute*; 2000; 28:399-405.

Dale et al.; "Laser Ignited Internal Combustion Engine—An Experimental Study"; *SAE 780329*; Feb./Mar. 1978.

Konorov et al.; "Laser Breakdown with Millijoule Trains of Picosecond Pulses Transmitted Through a Hollow-Core Photonic-Crystal Fibre"; *J. Physics D: Appl. Phys.*; 2003; 36:1375-1381.

Sato et al.; "Hollow-Waveguide-Based Transmission of Q-Switched Nd:YAG Laser Beam for Biological Tissue Ablation"; *SPIE Conference on Specialty Fiber Optics for Medical Applications*, San Jose, CA, *SPIE*; Jan. 1999; 3596:50-54.

Sato et aol. "Vacuum-Cored Hollow Waveguide for Transmission of High-Energy, Nanosecond Nd:YAG Laser Pulses and Its Application to Biological Tissue Ablation"; *Optics Letters*; 2000; 25(1):49-51.

Su et al.; "Beam Delivery By Large-Core Fibers: Effect of Launching Conditions on Near-Field Output Profile"; *Applied Optics*; Sep. 1992; 31(27):5816-5821.

Allison et al.; "Pulsed Laser Damage to Optical Fibers"; *Applied Optics*; 1985; 24(19):3140-3145.

Phuoc; "Laser Spark Ignition: Experimental Determination of Laser-induced Breakdown Thresholds of Combustion Gases"; *Optics Communications*; 2000; 175:419-423.

Matsuura et al.; "Hollow Fibers for Delivery of Harmonic Pulses of Q-Switched Nd:YAG Lasers"; *Applied Optics*; Jan. 2002; 41(3):442-445.

Matsuura et al.; "Hollow-Fiber Delivery of High-Power Pulsed Nd: YAG Laser Light"; *Optics Letters*; Dec. 1998; 23(23):1858-1860.

Phuoc et al.;"Optical Characterization of the Laser-induced Spark In Air," *Optical Diagnostics in Engineering*; 2001; 5:12-26.

Ferioli, et al., "Laser-Induced Breakdown Spectroscopy for On-Line Engine Equivalence Ratio Measurements," *Applied Spectroscopy*; 2003; 57(9):1183-1189.

Morrell, et al.; "Interpretation of Optical Emissions for Sensors in Liquid Fueled Combustors"; *AIAA, Paper No. 2001-0787*; 2001; pp. 1-12.

Mitchell et al.; "Formaldehyde Formation in Large Bore Natural Gas Engines Part 1: Formation Mechanisms"; *Journal of Engineering for Gas Turbines and Power*; 2000; 122:603-610.

Olsen et al.; "Formaldehyde Formation in Large Bore Engines Part 2: Factors Affecting Measured $CH_2O$"; *Journal of Engineering for Gas Turbines and Power*; Oct. 2000; 122:611-616.

Frendi et al.; "Dependence of Minimum Ignition Energy on Ignition Parameters"; *Combustion Science and Technology*; 1990; 73:395-413.

Blanc et al.; "Ignition of Explosive Gas Mixtures by Electric Sparks. 1. Minimum Ignition Energies and Quenching Distances of Mixtures of Methane, Oxygen and Inert Gases"; *The Journal of Chemical Physics*; 1947; 14(11):798-802.

DeMichelis; "Laser Induced Gas Breakdown: A Bibliographical Review"; *IEEE Journal of Quantum Electronics*; 1969; QE-5(4):188-202.

Fenn; "Lean Flammability Limit and Minimum Spark Ignition Energy"; *Industrial and Engineering Chemistry*; 1951; 43(12):2865-2869.

Ballal et al.; "The Influence of Flow Parameters on Minimum Ignition Energy and Quenching Distance"; *Proceedings of Fifteenth International Symposium on Combustion*; 1974; pp. 1473-1481.

Kim et al.; "Computational Modeling of Natural Gas Injection in a Large Bore Engine"; *J. Of Engineering for Gas Turbines and Power*; 2004; 126:656-664.

Kirkpatrick et al.; "Analytical and Computational Modeling of High-Pressure Gas Injection"; *Proceedings ASME ICE Fall Technical Conference, Paper No. 2001-ICE-410*; 2001; vol. 37-2, pp. 25-32.

Phuoc et al.; 2002; "Laser-induced Spark for Measurements of the Fuel-to-Air Ratio of a Combustible Mixture,"*Fuel*; 81, pp. 1761-1765.

Harilal et al.; "Diagnostics of Laser Induced Spark in Air Using Fast ICCD Photography"; *Internal Lab Report, Paper No. UCSD-LPLM-02-01, Fusion Division Center for Energy Research*, University of California, San Diego, CA; 2002.

Schnieder; "Techniques and Applications of Laser Spark Spectroscopy"; *Laser 83 Conference Proceedings*; 1982.

Ottesen et al.; "Real-Time Laser Spark Spectroscopy of Particulates in Combustion Environments"; *Applied Spectroscipy*; 1989; 43(6):967-976.

Chan et al.; "Spectrum Estimation and Noise Reduction for Laser Induced Breakdown Spectroscopy"; *MS State DSP Conference, Spectral Analysis Group: LIBS*; Fall 1995; pp. 21-33.

Furlong et al. "Combustion Control Using a Multiplexed Diode-Laser Sensor System"; *American Institute of Aeronautics and Astronautics*; 1996; p. 1-6.

Armstrong et al. "Spectroscopic Investigation of Laser-Initiated Low-Pressure Plasma in Atmospheric Gases"; *Applied Optics*; 1983; 22(10):1573-1577.

Phuoc et al.; "Laser Spark Ignition of a Jet Diffusion Flame"; *Combustion and Flame*, date unknown.

Forsich et al.; "Characterization of Laser-Induced Ignition of Biogas-Air Mixtures"; *Biomass and Energy*; 2004 27:299-312.

Dors et al.; "Fluid Dynamics Effects Following Laser-Induced Optical Breakdown"; *AIAA 2000-0717*; 2000.

Lackner et al.; "In Situ Investigation of Laser-Induced Ignition and the Early Stages of Methane-Air Combustion at High Pressures Using a Rapidly Tuned Diode Laser at 2.55 μm"; *Spectrochimica Acta Part A*; 2003; 59:2997-3018.

Kopecek et al.; "Laser-Induced Ignition of Methane-Air Mixtures at Pressures Up To 4 MPa"; *Laser Physics*; 2003; 13(11):1365-1369.

Kravchik et al.; "Numerical Modeling of Spark Ignition and Flame Initiation in a Quiescent Methane-Air Mixture"; *Combustion and Flame*; 1994; 99:635-643.

Borghese et al.; "Time-Resolved Spectral and Spatial Description of Laser-Induced Breakdown in Air as a Pulsed, Bright, and Broadband Ultraviolet-Visible Light Source"; *Applied Optics*; 1998; 37(18):3977-3981.

Maas et al.; "Observation and Simulation of Laser-Induced Ignition Processes in $O_2$-$O_3$ and $H_2$-$O_2$ Mixtures"; *Twenty-First Symposium (International) on Combustion/The Combustion Institute*; 1986; pp. 1869-1876.

Forch et al.; "Laser-Based Ignition of $H_2/O_2$ and $D_2/O_2$ Premixed Gases Through Resonant Multiphoton Excitation of H and D Atoms Near 243 nm"; *Combustion and Flame*; 1991; 85:254-262.

Van Stryland et al.; "Pulse-Width and Focal-Volume Dependence of Laser-Induced Breakdown"; *Physical Review B*; 1981; 23(5):2144-2151.

Willems et al.; "Modeling the Initial Growth of the Plasma and Flame Kernel in SI Engines"; *ICE* vol. 2001, 36-2 *ASME* 2001; p. 1-7.

Forch et al.; "Ultraviolet Laser Ignition of Premixed Gases by Efficient and Resonant Multiphoton Photochemical Formation of Microplasmas"; *Combustion Science and Technology*; 1987; 52:151-159.

Trott; "$CO_2$—Laser-Induced Deflagration of Fuel/Oxygen Mixtures[a]"; *J. Appl. Phys.*; 1983; 54(1):118-130.

Sloane; "Energy Requirements for Spherical Ignitions in Methane-Air Mixtures at Different Equivalence Ratios"; *Combustion Science and Technology*; 1990; 73:351-365.

Weinberg et al.; "A Preliminary Investigation of the Use of Focused Laser Beams for Minimum Ignition Energy Studies"; *Proc. Roy. Soc. Lond. A.*; 1971; 321:41-52.

Santavicca et al.; "Laser Induced Spark Ignition of Methane-Oxygen Mixtures"; *First Technical Report for NASA Grant NAG3-966*; 1991.

Schmieder; Laser Spark Ignition and Extinction of a Methane-Air Diffusion Flame; *J. Appl. Phys.*; 1981; 52(4):3000-3003.

Lavid et al.; "Photochemical Ignition of Premixed Hydrogen/Oxygen Mixtures with ArF Laser"; *Combustion Science and Technology*; 1994; 96:231-245.

Hardalupas et al.; "Chemiluminescence Sensor for Local Equivalence Ratio of Reacting Mixtures of Liquid Fuel Vapor and Air (Mast B Liquid)" www.Cheng.cam.ac.uk/research/groups/la; pp. 1-12, no date.

Morsy et al.; "Laser-Induced Ignition Using a Conical Cavity in $CH_4$/Air Mixtures"; *Combustion and Flame*; 1999; 119:473-482.

Morsy et al.; "Laser-Induced Two-Point Ignition of Premixture With a Single-Shot Laser"; *Combustion and Flame*; 2001; 125:724-727.

Gupta et al.; "Laser Based Ignition for Reciprocating Natural Gas Engines: Preliminary Experimental Study"; *Argonne National Laboratory, LBIS Round Table Meeting*; 2002.

Kohse-Höinghaus et al.; "Combustion at the Focus: Laser Diagnostics and Control"; *Proceedings of the Combustion Institute*; 2005; 30:89-123.

Thiele et al.; "Numerical Simulation of Spark Ignition Including Ionization"; *Proceedings of the Combustion Institute*; 2000; 28:1177-1185.

Yasar; "A New Ignition Model for Spark-Ignition Engine Simulations"; *Parallel Computing*; 2001; 27:179-200.

Herdin et al.; "Laser Ignition a New Concept to Use and Increase the Potentials of the Gas Engines"; *General Electric, 2nd Annual Advanced Stationary Reciprocating Engines Conference*; 2005, pp. 1-35.

Starik et al.; "Possibility of Initiation of Combustion of $CH_4$-$O_2$ (Air) Mixtures with Laser-Induced Excitation of $O_2$ Molecules"; *Combustion, Explosion, and Shock Waves*; 2004; 40(5):499-510.

Zizak; "Flame Emission Spectroscopy: Fundamentals and Applications"; *ICS Training Course on Laser Diagnostics and Combustion Processes*; Nov. 2000.

Yuasa; "Effects of Energy Deposition Schedule on Minimum Ignition Energy in Spark Ignition of Methane/Air Mixtures"; *Proceedings of the Combustion Institute*; 29:743-750.

Beretta et al.; "Turbulent Flame Propagation and Combustion in Spark Ignition Engines"; *Combustion and Flame*; 1983; 52:217-245.

Simmie; "Detailed Chemical Kinetic Models for the Combustion of Hydrocarbon Fuels"; *Progress in Energy and Combustion Science*; 2003; 29:599-634.

Gatowski et al.; "Flame Photographs in a Spark-Ignition Engine"; *Combustion and Flame*; 1984; 56:71-81.

Richou et al.; "Delivery of 10-MW Nd:YAG Laser Pulses by Large-Core Optical Fibers: Dependence of the Laser-Intensity Profile on Beam Propagation"; *Applied Optics*; Mar. 1997; 36(7):1610-1614.

Alda et al.; "Characterization of Aberrated Laser Beams"; *J. Opt. Soc. Am. A.*; 1997; 14(10):2737-2747.

Green; "Beam Focusability Factor—A New Monitoring Tool for Increased Profitability"; *Lasers in Manufacturing*; 2002; vol. 28.

Koplow et al.; "Single-Mode Operation of a Coiled Multimode Fiber Amplifier"; *Optics Letters*; 2000; 25(7):442-444.

Potyrailo et al.; "Near-Ultraviolet Evanescent-Wave Absorption Sensor Based on a Multimode Optical Fiber"; *Analytical Chemistry*; 1998; 70:1639-1645.

Galvanauskas; "High Power Fiber Lasers"; *Optics and Photonics News*; 2004; pp. 42-47.

Hand et al.; "Fibre Optic Beam Delivery System for High Peak Power Laser PIV Illumination"; *Meas. Sci. Technol.*; 1999; 10:239-245.

Trott et al.; "High-Power Nd: Glass Laser Transmission Through Optical Fibers and Its Use in Acceleration of Thin Foil Targets"; *J. Applied Physics*; 1990; 67(7):3297-3301.

Hongo et al.; "Transmission of Kilowatt-Class $CO_2$ Laser Light Through Dielectric-Coated Metallic Hollow Waveguides for Material Processing"; *Applied Optics*; 31(24):5114-5120.

Hunter et al.; "Selecting a High-Power Fiber-Optic Laser Beam Delivery System"; *Laser Institute of America, Proceedings ICALEO*; 1996; 81E:173-182.

Schmidt-Uhlig et al.; "New Simplified Coupling Scheme for the Delivery of 20 MW Nd: YAG Laser Pulses by Large Core Optical Fibers"; *Applied Physics B*; 2001; 72:183-186.

Moulton; "New Technologies of Solid State Lasers for Materials Processing"; *Q-Peak Applied Photonic Systems*; 2004.

Moar et al.; "Fabrication, Modeling, and Direct Evanescent Field Measurement of Tapered Optical Fiber Sensors"; *Journal of Applied Physics*; 1999; 85(7):3395-3398.

Matsuura et al.; "Optical Properties of Small-Bore Hollow Glass Waveguides"; *Applied Optics*; 1995; 34(30):6842-6847.

Dai et al.; "High-Peak-Power, Pulsed $CO_2$ Laser Light Delivery by Hollow Glass Waveguides"; *Applied Optics*; 1997; 36(21):5072-5077.

Mohebbi et al.; "Silver-Coated Hollow-Glass Waveguide for Applications at 800 nm"; *Applied Optics*; 2002; 41(33):7031-7035.

Bihari et al.; "Development of Advanced Laser Ignition System for Stationary Natural Gas Reciprocating Engines"; *ASME, Paper ICEF2005-1325*; 2005; pp. 1-8.

Siegman; "Analysis of Laser Beam Quality Degradation Caused by Quartic Phase Aberrations"; *Applied Optics*; 1993; 32(30):5893-5901.

Sturm et al.; "Optical Fiber Transmission of Multiple Q-Switch Nd: YAG Laser Pulses with Microsecond Interpulse Separations"; *Applied Physics B*; 1996; 63:363-370.

International Search Report for International (PCT) Patent Application No. PCT/US05/27894, mailed Apr. 30, 2007.

Written Opinion for International (PCT) Patent Application No. PCT/US05/27894, mailed Apr. 30, 2007.

Official Action for U.S. Appl. No. 11/126,908, mailed Apr. 4, 2007.

Official Action for U.S. Appl. No. 11/197,832, mailed Mar. 2, 2007.

Abdel-Gayed et al.; Criteria for Turbulent Propagation Limits of Premixed Flames; *Combustion and Flame*; 1985; 62:61-68.

Ahrens et al; Development of an Open Path Laser Ignition System for a Large Bore Natural Gas Engine: Part 2 Single Cylinder Demonstration; *ASME*; 2005 Fall Technical Conference ICEF2005 Proceedings; ICES2005-1317:1-9.

Alda et al; Characterization of Aberrated Laser Beams; *Optical Society of America*; 1997; 14(10):2737-2747.

Ballal et al; The Influence of Flow Parameters on Minimum Ignition Energy and Quenching Distance; *Proceedings of Fifteenth International Symposium on Combustion*; 1974; 1473-1481.

Beduneau et al; Measurements of Minimum Ignition Energy in Premixed Lamina Methane/Air Flow by Using Laser Induced Spark; *Combustion and Flame*; 2003; 132:653-665.

Beretta et al; Turbulent Flame Propagation and Combustion in Spark Ignition Engines; *Combustion and Flame*; 1983; 52:217-245.

Bihari et al; Development of Advanced Laser Ignition System for Stationary Natural Gas Reciprocating Engines; *ASME*; 2005 Fall Technical Conference ICEF2005 Proceedings; ICEF2005-1325:1-8.

Biruduganti et al; Performance Analysis of a Natural Gas Generator Using Laser Ignition; *ASME*; 2004 Fall Technical Conference ICEF04; ICEF2004-983:1-7.

Borghi, R.; On the Structure and Morphology of Turbulent Premixed Flames: *Recent Advances in Aerospace Sciences; in Honor of Luigi Crocco on His Seventy-Fifth Birthday*; 1985; Chapter 7:117-138.

Bradley et al; Fundamentals of High-Energy Spark Ignition with Lasers; *Combustion and Flame*; 2004;138:55-77.

Bradley et al; Spark Ignition and the Early States of Turbulent Flame Propagation; *Combustion and Flame*; 1987; 69:71-93.

Bradley et al; The Measurement of Laminar Burning Velocities and Markstein Numbers for Iso-octane-Air and Iso-octane-n-Heptane-Air Mixtures at Elevated Temperatures and Pressures in an Explosion Bomb; *Combustion and Flame*; 1998; 115:126-144.

Buchter, S.; Advances Lead to Miniature Supercontinuum Sources; *Photonics Spectra*; 2004;38(10):46,49.

Chen et al; Spatial and Temporal Profiles of Pulsed Laser-Induced Air Plasma Emissions; *Journal of Quantitative Spectroscopy & Radiative Transfer*; 2000; 67:91-103.

Chen et al; Visualization of Laser-Induced Breakdown and Ignition; *Optics Express*; 2001; 9(7):360-372.

Dai et al; High-Peak-Power, Pulsed $CO_2$ Laser Light Delivery by Hollow Glass Waveguides; *Applied Optics*;1997; 36(21):5072-5077.

Davis et al; Laser-Induced Plasma Formation in Xe, Ar, $N_2$, and $O_2$ at the First Four Nd:YAG Harmonics; *Applied Optics*; 1991; 30(30):4358-4364.

Dors et al; Computational Fluid-Dynamic Model of Laser-Induced Breakdown in Air; *Applied Optics*; 2003; 42(30):5978-5985.

Forsich et al; Characterization of Laser-Induced Ignition of Biogas-Air Mixtures; *Biomass & Bioenergy*; 2004; 27:299-312.

Galt et al; Optical Breakdown in Fused Silica and Argon Gas: Application to Nd:YAG Laswer Limiter; *Applied Optics*; 2003; 42(3):579-584.

Galvanauskas, A.; High Power Fiber Lasers; *Optics & Photonics News*; 2004; Jul.:42-47.

Gamal et al; A Numerical Investigation of the Dependence of the Threshold Irradiance on the Wavelength in Laser-Induced Breakdown in $N_2$; *J. Phys. D: Appl. Phys*; 1999; 32:423-429.

Gatowski et al; Flame Photographs in a Spark-Ignition Engine; *Combustion and Flame*; 1984; 56:71-81.

Glumac et al; Temporal and Spatial Evolution of a Laser Spark in Air; *AIAA Journal*; 2005; 43(9):1984-1993.

Green, L.; Beam Focusability Factor—A New Monitoring Tool for Increased Profitability; *Lasers in Manufacturing, The Industrial Laser User*; 2002; 28:2 pages.

Hand et al; Fibre Optic Beam Delivery System for High Peak Power Laser PIV Illumination; *Meas. Sci. Technol.*; 1999; 10:239-245.

Herdin et al; Laser Ignition—A New Concept to Use and Increase the Potentials of Gas Engines; *ASME*; 2005 Fall Technical Conference Proceedings of ICEF2005; ICEF2005-1352:1-9.

Herdin, G.; Laser Ignition a New Concept to Use and Increase the Potentials of the Gas Engines; *GE Jenbacher*; 2005; 35 pages.

Hongo et al; Transmission of Kilowatt-Class $CO_2$ Laser Light Through Dielectric-Coated Metallic Hollow Waveguides for Material Processing; *Applied Optics*; 1992; 31(24):5114-5120.

Hunter, et al; Selecting a High-Power Fiber-Optic Laser Beam Delivery System; *Laser Institute of America*; 1996; 81E:173-182.

Gaborel et al; Toward the Development of a Laser Ignition System for Aircraft Engines; *1st Workshop INCA*, Villaroche, France; 2005; 1-8.

Kaminski et al; Spark Ignition of Turbulent Methane/Air Mixtures Revealed by Time-Resolved Planar Laser-Induced Fluorescence and Direct Numerical Simulations; *Proceedings of the Combustion Institute*; 2000; 28:399-405.

Klett et al; Ignition Characteristics of Methane-air Mixtures Established Using a Rapid Compression Machine; *Argonne National Laboratory*; 2005 ASRE Meeting; 28 pages.

Kliner et al; Fiber Laser Technology Reels in High Power Results; *SPIE's oemagazine*; 2004; January:32-35.

Kohse-Hoinghaus et al; Combustion at the Focus: Laser Diagnostics and Control; *Proceedings of the Combustion Institute*; 2004; 30:89-123.

Kono et al; Mechanism of Flame Kernel Formation Produced by Short Duration Sparks; *Twenty-Second Symposium (International) on Combustion/The Combustion Institute*; 1988; 1643-1649.

Konorov et al; Laser Breakdown with Millijoule Trains of Picosecond Pulses Transmitted Through a Hollow-Core Photonic-Crystal Fibre; *Journal of Physics D*; 2003; 36:1375-1381.

Kopecek et al; Laser Ignition of Methane-Air Mixtures at High Pressures; *Experimental Thermal and Fluid Science*; 2003; 27:499-503.

Kopecek et al; Laser Ignition of Methane-Air Mixtures at High Pressures and Diagnostics; *Journal of Engineering for Gas Turbines and Power*; 2005; 127:213-219.

Koplow et al; Single-Mode Operation of a Coiled Multimode Fiber Amplifier; *Optics Letters*; 2000; 25(7):442-444.

Kravchik et al; From Spark Ignition to Flame Initiation; *Combust. Sci. And Tech.*; 1995; 108:1-30.

Lackner et al; Investigation of the Early Stages in Laser-Induced Ignition by Schlieren Photography and Laser-Induced Fluorescence Spectroscopy; *Optics Express*; 2004; 12(19):4546-4557.

Lackner et al; Laser Ignition in Internal Combustion Engines—A Contribution to a Sustainable Environment; *Institute of Chemical Engineering*; no date; 18 pages.

Lee et al; Laser Spark Ignition of Chemically Reactive Gases; *AIAA Journal*; 7(2):312-317, 1969.

Liedl et al; Laser Induced Ignition of Gasoline Direct Injection Engines; *Institute for Forming- and High Power Laser Technology*; no date; Arsenal Obj. 207(1030):6 pages.

Limpert et al; 100-W Average-Power, High-Energy Nanosecond Fiber Amplifier; *Applied Physics B*; 2002; 75:477-479.

Longenecker et al; Laser-Generated Spark Morphology and Temperature Records from Emission and Rayleigh Scattering Studies; *Applied Optics*; 2003; 42(6):990-996.

McMillian et al; Laser Spark Ignition: Laser Development and Engine Testing; *ASME*; 2004 Fall Technical Conference ICEF04 Proceedings; ICEF2004-917:1-10.

Maly, R.; Spark Ignition: Its Physics and Effect on the Internal Combustion Engine; *Fuel Economy in Road Vehicles Powered by Spark Ignition Engines*; 1984; Chapters 3-4:91-149; Figs 1-16B.

Maly et al; Initiation and Propagation of Flame Fronts in Lean $CH_4$-Air Mixtures by the Three Modes of the Ignition Spark; *Inhibition and Ignition (Proceedings of Seventeenth International Symposium on Combustion)*; 1976; 821-831.

Matsuura et al; Hollow-Fiber Delivery of High-Power Pulsed Nd:YAG Laser Light; *Optics Letters*; 1998; 23(23):1858-1860.

Matsuura et al; Hollow Fibers for Delivery of Harmonic Pulses of Q-Switched Nd:YAG Lasers; *Applied Optics*; 2002; 41(3):442-445.

Matsuura et al; Low Order Multimode Generation in Hollow Glass Waveguides; *Electronics Letters*; 1996; 32(12):1096-1098.

Matsuura et al; Optical Properties of Small-Bore Hollow Glass Waveguides; *Applied Optics*; 1995; 34(30):6842-6847.

Moar et al; Fabrication, Modeling, and Direct Evanescent Field Measurement of Tapered Optical Fiber Sensors; *Journal of Applied Physics*; 1999; 85(7):3395-3398.

Mohebbi et al; Silver-Coated Hollow-Glass Waveguide for Applications at 800 nm; *Applied Optics*; 2002; 41(33):7031-7035.

Morgan, C.G.; Laser-Induced Breakdown of Gases; *Rep. Prog. Phys.*; 1975; 38:621-665.

Morsy et al; Numerical Simulation of Front Lobe Formation in Laser-Induced Spark Ignition of $CH_4$/Air Mixtures; *Proceedings of the Combustion Institute*; 2002; 29:1613-1619.

Moulton, P.; New Technologies of Solid State Lasers for Materials Processing; *Q-Peak Applied Photonic Systems*; 2004 (PhAST); 50 pages.

Niemz, M.H.; Threshold Dependence of Laser-Induced Optical Breakdown on Pulse Duration; *Appl. Phys. Lett.*; 1995; 66(10):1181-1183.

Nubling et al; Launch Conditions and Mode Coupling in Hollow-Glass Waveguides; *Optical Engineering*; 1998; 37(9):2454-2458.

Oriel Instruments; Light Collection and System Throughput; *Oriel Instruments Catalog/Light Sources*; no date; 1-19 through 1-15.

Phuoc, T.; A Comparative Study of the Photon Pressure Force, the Photophoretic Force, and the Adhesion Van Der Waals Force; *Optics Communications*; 2005; 245:27-35.

Phuoc, T.; An Experimental and Numerical Study of Laser-Induced Spark in Air; *Optics and Lasers in Engineering*; 2005; 43:113-129.

Phuoc et al; Laser-Induced Spark for Measurements of the Fuel-to-air Ratio of a Combustible Mixture; *Fuel*; 2002; 81:1761-1765.

Phuoc, T.; Laser-Induced Spark Ignition Fundamental and Applications; *Optics and Lasers in Engineering*; 2006; 44:351-397.

Phuoc et al; Laser-Induced Spark Ignition of $CH_4$/Air Mixtures; *Combustion and Flame*; 1999; 119:203-216.

Phuoc, T.; Laser Spark Ignition: Experimental Determination of Laser-Induced Breakdown Thresholds of Combustion Gases; *Optics Communications*; 2000; 175:419-423.

Phuoc, T.; Single-Point Versus Multi-Point Laser Ignition: Experimental Measurements of Combustion Times and Pressures; *Combustion and Flame*; 2000; 122:508-510.

Potyrailo et al; Near-Ultraviolet Evanescent-Wave Absorption Sensor Based on a Multimode Optical Fiber; *Analytical Chemistry*; 1998; 70(8):1639-1645.

Quader, A.; What Limits Lean Operation in Spark Ignition Engines—Flame Initiation or Propagation?;*SAE Transactions*; 1976; SAE Paper 760760:2374-2387.

Richardson et al; Laser Spark Ignition of a Blended Hydrogen-Natural Gas Fueled Single Cylinder Engine; *ASME*; 2006 Spring Technical Conference ICES2006 Proceedings; ICES2006-1397:1-9.

Richou et al; Delivery of 10-MW Nd:YAG Laser Pulses by Large-Core Optical Fibers: Dependence of the Laser-Intensity Profile on Beam Propagation; *Applied Optics*; 1997; 36(7):1610-1614.

Ronney, P.; Laser Versus Conventional Ignition of Flames; *Optical Engineering*; 33(2):510-521, 1994.

Rosen et al; Laser-Induced Breakdown in Nitrogen and the Rare Gases at 0.53 and 0.35 μm; *J. Phys. D.:Appl. Phys.*; 1987; 20:1264-1276.

Roundy, C.; Propagation Factor Quantifies Laser Beam Performance; *Laser Focus World/Beam Profile Analysis*; 1999; 3 pages.

Ruff et al; Measurement of Beam Quality Degradation Due to Spherical Aberration in a Simple Lens; *Optical and Quantum Electronics*; 1994; 26:629-632.

Sato et al; Hollow-Waveguide-Based Transmission of Q-Switched Nd:YAG Laser Beam for Biological Tissue Ablation; *SPIE Conference on Specialty Fiber Optics for Medical Applications*; 1999; SPIE 3596:50-54.

Sato et al; Vacuum-Cored Hollow Waveguide for Transmission of High-Energy, Nanosecond Nd:YAG Laser Pulses and its Application to Biological Tissue Ablation; *Optics Letters*; 2000; 25(1):49-51.

Schmidt-Uhlig et al; New Simplified Coupling Scheme for the Delivery of 20 MW Nd:YAG Laser Pulses by Large Core Optical Fibers; *Applied Physics B*; 2001; 72:183-186.

Shephard et al; Improved Hollow-Core Photonic Crystal Fiber Design for Delivery of nanosecond Pulses in Laser Micromachining Applications; *Applied Optics*; 2005; 44(21):4582-4587.

Siegman, A.E.; Analysis of Laser Beam Quality Degradation Caused by Quartic Phase Aberrations; *Applied Optics*; 1993; 32(30):5893-5901.

Siegman, A.E.; How to "Maybe" Measure Laser Beam Quality; *Optical Society of America Annual Meeting Tutorial Presentation*; 1997: October:18 pages.

Siegman, A.E.; How to (Maybe) Measure Laser Beam Quality; *CREOL*; 2004; April:50 pages.

Siegman et al; Output Beam Propagation and Beam Quality from a Multimode Stable-Cavity Laser; *IEEE Journal of Quantum Electronics*; 1993; 29(4):1212-1217.

Simmie, J.; Detailed Chemical Kinetic Models for the Combustion of Hydrocarbon Fuels; *Progress in Energy and Combustion Science*; 2003; 29:599-634.

Sircar et al; Laser Induced Breakdown of Ar, $N_2$ and $O_2$ gases using 1.064, 0.532, 0.355 and 0.266 μm Radiation; *Applied Physics B*; 1996; 63:623-627.

Sjoberg et al; Dependence of Stimulated Brillouin Scattering in Multimode Fibers on Beam Quality, Pulse Duration, and Coherence Length; *Optical Society of America*; 2003; 20(3):434-442.

Sloane, T.; Energy Requirements for Spherical Ignitions in Methane-Air Mixtures at Different Equivalence Ratios; *Combust. Sci. And Tech.*; 1990; 73:351-365.

Spiglanin et al; Time-Resolved Imaging of Flame Kernels: Laser Spark Ignition of $H_2/O_2$/Ar Mixtures; *Combustion and Flame*; 1995; 102:310-328.

Stachowicz et al; Design and Development of Waukesha's, Stoichiometric, Cooled EGR Engine for the California ARICE Program; *ASME*; 2005 Fall Technical Conference of ICEF2005 Proceedings; ICEF2005-1329:1-11.

Stakhiv et al; Laser Ignition of Engines Via Optical Fibers?; *Laser Physics*; 2004; 14(5):738-747.

Starik et al; Possibility of Initiation of Combustion of $CH_4$-$O_2$ (air) Mixtures with Laser-Induced Excitation of $O_2$ Molecules; *Combustion, Explosion, and Shock Waves*; 2004; 40(5):499-510.

Sturm et al; Optical Fiber Transmission of Multiple Q-Switch Nd:YAG Laser Pulses with Microsecond Interpulse Separations; *Applied Physics B*; 1996; 63:363-370.

Su et al; Beam Delivery by Large-Core Fibers: Effect of Launching Conditions on Near-Field Output Profile; *Applied Optics*; 1992; 31(27):5816-5821.

Tambay et al; Laser-Induced Breakdown Studies of Laboratory Air at 0.266, 0.355, 0.532, and 1.06 µm; *J. Appl. Phys.*; 1991; 70(5):2890-2892.

Thiele et al; Numerical Simulation of Spark Ignition Including Ionization; *Proceedings of the Combustion Institute*; 2000; 28:1177-1185.

Tran et al; Optical Characterization of the Laser-Induced Spark in Air; *National Energy Technology Laboratory U.S. Department of Energy*; no date; 1-14.

Trinh et al; Dual-Laser-Pulse Ignition; *Photonics Tech Briefs*; 2006; January:14a, 15a.

Trott et al; High-Power Nd:Glass Laser Transmission Through Optical Fibers and its Use in Acceleration of Thin Foil Targets; *J. Appl. Phys.*; 1990; 67(7):3297-3301.

Turcu et al; Measurement of KrF Laser Breakdown Threshold in Gases; *Optics Communications*; 1997; 134:66-68.

Tzortzakis et al; Femtosecond Laser-Guided Electric discharge in Air; *Laboratoire d'Optique Appliquee*; no date; CNRS UMR 7639: 2 pages.

Van Stryland et al; Pulse-Width and Focal-Volume Dependence of Laser-Induced Breakdown; *Physical Review B*; 1981; 23(5):2144-2151.

Weinrotter et al; Laser Ignition of Ultra-Lean Methane/Hydrogen/Air Mixtures at High Temperature and Pressure; *Experimental Thermal and Fluid Science*; 2005; 29:569-577.

Williams et al; Picosecond Air Breakdown Studies at 0.53 µm; *Appl. Phys. Lett.*; 1983; 43(4):352-354.

Yalin et al; Development of a Fiber Delivered Laser Ignition System for Natural Gas Engines; *ASME*; 2006 Spring Technical Conference ICES2006 Proceedings; ICES2006-1370:1-6.

Yalin et al; Laser Ignition of Natural Gas Engines Using Fiber Delivery; *ASME*; 2005 Fall Technical Conference ICEF2005 Proceedings; ICEF2005-1336:1-9.

Yasar, O.; A New Ignition Model for Spark-Ignited Engine Simulations; *Parallel Computing*; 2001; 27:179-200.

Yuasa et al; Effects of Energy Deposition Schedule on Minimum Ignition Energy in Spark Ignition of Methane/Air Mixtures; *Proceedings of the Combustion Institute*; 2002; 29:743-750.

Zizak, G.; Flame Emission Spectroscopy: Fundamentals and Applications; *ICS Training Course on Laser Diagnostics of Combustion Processes, NILES*, University of Cairo, Egypt; 2000; November:29 pages.

Gaborel, G. et al., "Toward the Development of a Laser Ignition System for Aircraft Engines." Oct. 2005, pp. 1-8.

Parry, J. et al., "Analysis of Optical Damage Mechanisms in Hollow Core Waveguides Delivering Nanosecond Pulses From a Q-Switched Nd:YAG Laser." Published by OSA. Doc. id 71526, Posted Aug. 2006, pp. 1-33.

\* cited by examiner

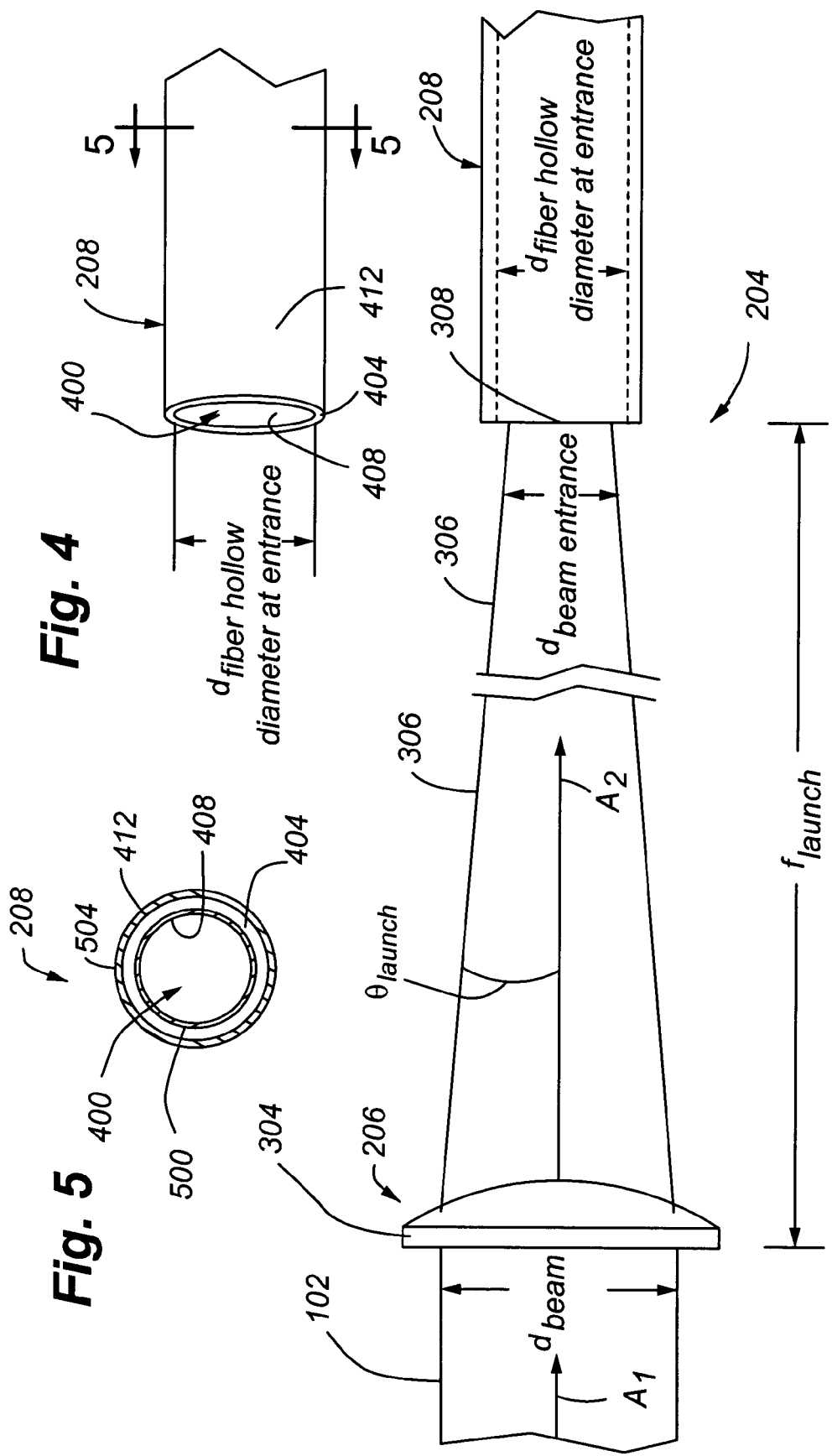

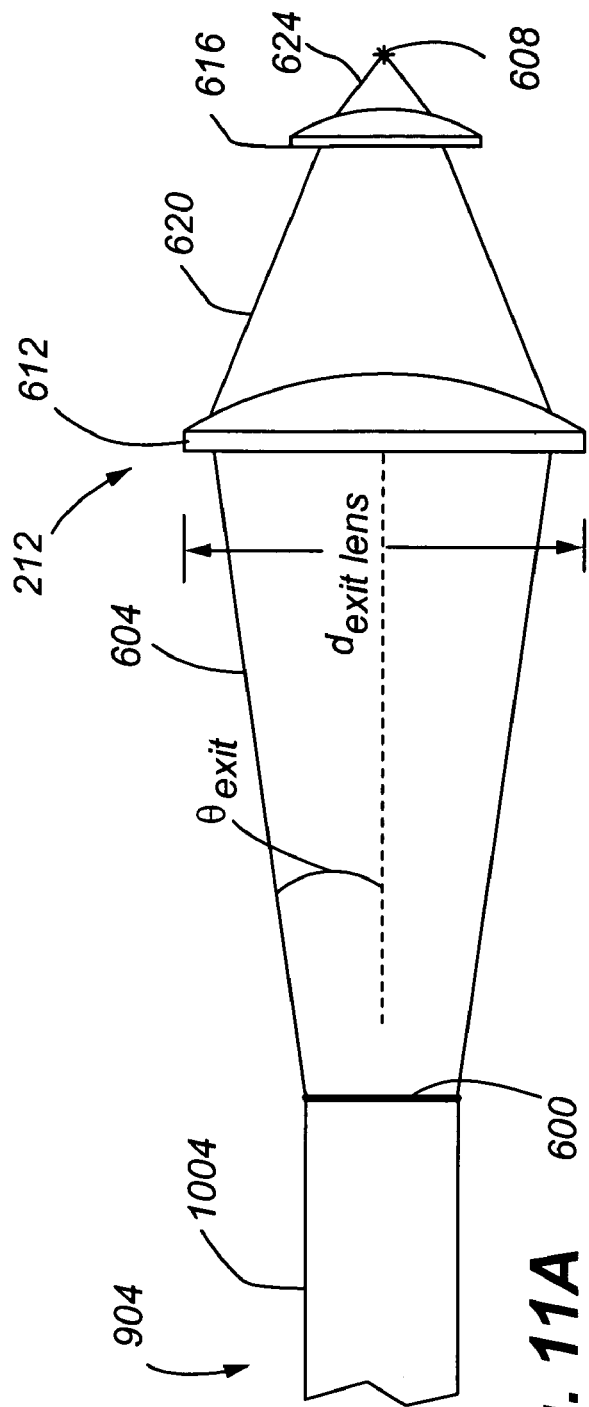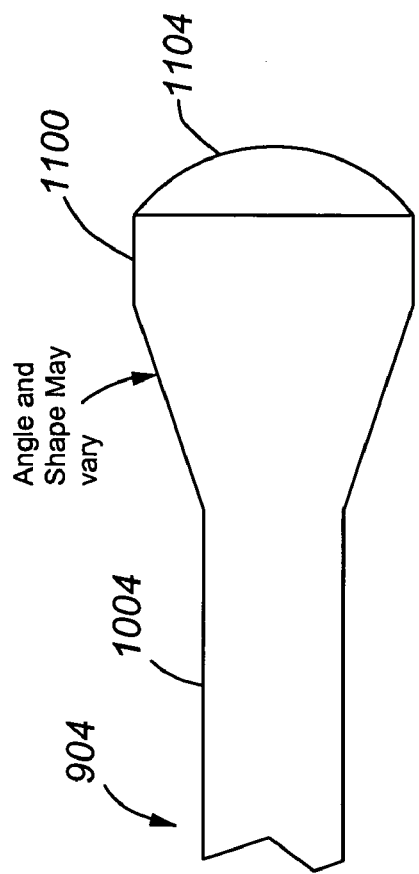
Fig. 11A
Fig. 11B ly increases in the cylinder, the breakdown voltage (minimum voltage required to form a spark using a spark ignition system) also increases, ultimately to such high voltage levels that traditional spark ignition systems encounter problems with dielectric breakdown leading to unwanted sparking from the ignition leads and other undesired locations (i.e., the spark does not form between the electrodes as intended). Even if the high voltage can be managed, high voltage means that electrode erosion can be quite high. The combination of spark plug erosion and dielectric breakdown is a limiting factor in the operational envelope of modern gas engines. Optical sparks suffer from neither of these shortcomings and thus may have significant advantages for improved engine operation. In certain cases, optical sparks can also afford performance benefits associated with extension of maintenance intervals as well as changes in the lean limit, coefficient of variation of pressure, pollutant emissions, and other parameters.

OPTICAL DIAGNOSTICS INTEGRATED WITH LASER SPARK DELIVERY SYSTEM

CROSS REFERENCE TO RELATED APPLICATIONS

The present application is a continuation-in-part application of U.S. patent application Ser. No. 11/126,908 filed May 10, 2005, which claimed the benefit of U.S. Provisional Patent Application No. 60/598,932 filed on Aug. 4, 2004; in addition, the present application claims the benefit of U.S. Provisional Patent Application No. 60/598,932 filed on Aug. 4, 2004. The entire disclosures of the above-referenced patent applications are incorporated herein by reference in their entirety. Cross reference is also made to U.S. Patent Application Ser. No. 11/197,832 filed on Aug. 4, 2005 now U.S. Pat. No. 7,340,129, entitled "FIBER LASER COUPLED OPTICAL SPARK DELIVERY SYSTEM", the entire disclosure of which is incorporated herein by reference in its entirety.

STATEMENT REGARDING FEDERALLY SPONSORED RESEARCH OR DEVELOPMENT

This invention was made with United States Government support under Grant No. DE-FC26-02NT41335 awarded by the Department of Energy. The United States Government may have certain rights in the invention.

FIELD OF THE INVENTION

The present invention relates to a system for generating a spark and/or performing diagnostics on a light, such as a spark and/or a flame, such as within a cylinder of an engine.

BACKGROUND OF THE INVENTION

Pulsed lasers producing optical pulses with short temporal duration and high peak powers may be used to create laser sparks and initiate combustion. When the pulsed laser beam is focused to a small point, the intensity (power per area) at that point can be large enough to initiate electrical breakdown in the gas, thereby forming a spark (plasma). The physical mechanisms postulated for breakdown include photochemical absorption, multi-photon ionization, and electron cascade.

In an electron cascade, it is assumed that a small number of electrons appear in the beam focus region. These electrons acquire energy from the electric field by absorption of photons, and collide with neutral atoms, a process termed "inverse bremsstrahlung". The electrons ionize the gas when their energy exceeds the ionization potential of the atoms. The electron collision will ionize the atom, producing additional electron(s) to start the cascade process and lead to avalanche breakdown.

The minimum amount of energy or intensity required to cause the breakdown is commonly referred to as the breakdown threshold. For nano second pulse durations and milli joule energy levels, breakdown is thought to be intensity limited. In addition, the breakdown threshold is also dependent on the gas composition and pressure existing in the spark target environment.

Experimental measurements of spatially and temporally averaged optical intensities are found by dividing the laser power (pulse energy/pulse duration) by the beam area. At the spark location the beam area is typically small, with dimensions on the order of 10 to 100 µm, and in many experiments it has not been precisely measured. Therefore, there tends to be some uncertainty in published intensity requirements for breakdown and spark formation. Additional uncertainty intensity requirements is due to spatial and temporal averaging. For conditions of interest, including nano second pulse durations and milli joule energy levels with a target sparking environment comprising low-particulate (or particulate free) gas mixtures with a significant fraction of air and pressures of approximately 1 to 30 atmospheres, the required optical intensity to spark is approximately 0.5 to $10 \times 10^{11}$ W/cm$^2$.

For sparking uses associated with combustion engines, the desired combination of lean mixtures and high brake mean effective pressure results in the cylinder pressure and mixture density in modern engines being relatively high, creating difficulties for traditional spark ignition systems. As the density increases in the cylinder, the breakdown voltage (minimum voltage required to form a spark using a spark ignition system) also increases, ultimately to such high voltage levels that traditional spark ignition systems encounter problems with dielectric breakdown leading to unwanted sparking from the ignition leads and other undesired locations (i.e., the spark does not form between the electrodes as intended). Even if the high voltage can be managed, high voltage means that electrode erosion can be quite high. The combination of spark plug erosion and dielectric breakdown is a limiting factor in the operational envelope of modern gas engines. Optical sparks suffer from neither of these shortcomings and thus may have significant advantages for improved engine operation. In certain cases, optical sparks can also afford performance benefits associated with extension of maintenance intervals as well as changes in the lean limit, coefficient of variation of pressure, pollutant emissions, and other parameters.

Laser ignition has been shown to be a particularly effective way of igniting lean mixtures. It is fairly easy to create a spark by using "open path" laser delivery. The open path method implies that the laser beam propagates through the ambient air and is steered to the desired location by mirrors. Although simple and effective, this system is not practical for most industrial applications. Thus, there is a need for development and demonstration of a fiber optic delivery system.

The key challenges associated with the use of fiber optic delivery are the intensity damage threshold of the fiber optic material and limitations on focusing fiber optically delivered light. The former point relates to material properties of fiber material, typically silica, and limits the maximum achievable optical intensity at the fiber exit to approximately 1 to $5 \times 10^9$ W/cm$^2$. Generally, the desired spark location is not right at the fiber exit, but is located some distance downstream of the fiber exit, so that intermediate optics are used to capture the light leaving the fiber and to focus it at the desired spark location. Because the intensity at the fiber exit is limited, the imaging or focusing requirements to generate a sufficient intensity to spark at the desired spark location become more stringent. In other words, the light exiting the fiber must be demagnified to enable a sufficiently high optical intensity that exceeds the breakdown threshold at the desired spark location.

The problem is compounded by the second challenge which is the difficulty in focusing fiber optically delivered light. The minimum achievable spot size (i.e. beam dimension at the focal spot) tends to increase for a laser beam that has passed through a fiber optic. This increase in spot size, which makes it more difficult to reach high intensity, is related to a degradation of the spatial quality of a laser beam caused by transmission through a fiber. The spatial quality of a laser beam, typically characterized by its $M^2$ parameter, is a function of the transverse spatial modes of which the beam is composed. (A low $M^2$ parameter corresponds to a beam composed of "lower order" spatial modes, and such modes can be focused to smaller dimensions.) Generally, the $M^2$ parameter of the beam exiting the fiber is relatively large, and larger than the value for the beam entering the fiber. The spatial quality (and $M^2$) of light exiting a fiber is influenced by the fiber diameter and the exit angle of light leaving the fiber. For small-diameter single-mode fibers (diameter<~30 µm) the degradation is minimal; however, such fibers cannot transmit a large amount of energy and are not considered useful in laser ignition application(s). Larger diameter fibers are required to transmit higher energies, but in such cases the larger diameter increases the beam degradation and thus impedes focusing to small spot sizes (high intensities).

Solid core fiber optics have one optical material in the core (center channel) and a second optical material in the cladding (surrounding material). The index-of-refraction of the core material is selected to be larger than that of the cladding material so that light at the core-cladding interface is "totally internally reflected" and thus guided through the fiber core. Hollow core fibers have a hollow bore (no material) surrounded by a wall material. Such a configuration has a higher index in the wall than the core and does not allow efficient light guiding. Uncoated hollow fibers may only be effectively used in straight geometries.

It is noted that it is much more difficult to form a spark in the gas phase as compared to on a solid or in a liquid because more optical intensity is required. There are a number of papers/approaches that form sparks off solid surfaces after fiber delivery, and this can be done rather "routinely" with a solid fiber. For the same reason, it is also routine to spark in gases containing dust, sprays, or particulate matter since the spark initially forms on those liquids/solids as opposed to in the gas. However, it is desirable to spark in the gas phase because it allows the spark to be located away from cylinder walls or other solid surfaces, which act as heat sinks and yield poorer combustion performance. Freedom in locating the spark may also allow sparking at other locations that offer other combustion benefits (for example, locations where the air/fuel mixing is better or the gas velocity field is favorable).

Another consequence of the ease of sparking on solids is that the use of fiber optics becomes harder because of the tendency to spark (unwantedly) at the launch entrance of the fiber. Such sparks consume energy from the laser beam and may degrade the quality of the beam preventing subsequent sparking after the fiber.

In general, ordinary solid core fibers suffer from degradation of the quality of the laser light as it travels through them, as well as intensity limits and difficulties of launching the input light. Fiber lasers, however, may circumvent these problems and are capable of delivering high-quality and high-intensity laser pulses.

Diagnostics of the spark and/or combustion processes are useful for monitoring performance of the ignition system and monitoring engine combustion performance and parameters. U.S. Pat. No. 6,903,357, incorporated herein by reference in its entirety, provides a system for detecting sparks by using a solid state device, such as photodetector, for detecting the light energy generated by sparks. However, among other things, this reference fails to disclose the combination of providing a spark and measuring diagnostic light. Japanese Patent Nos. 63-90643 and 63-105261, incorporated herein by reference in their entirety, disclose the detection of an air-fuel ratio by measuring the spectra pattern or the intensity of total emissions. However, among other things, these references also fail to disclose the combination of providing a spark and measuring diagnostic light. U.S. Pat. No. 6,762,835, incorporated by reference herein in its entirety, discloses a solid silica core fiber for transmitting laser light and collecting the light from the spark created in a molten metal. However, solid silica core fibers are not suitable for generating a spark in air and/or in fuel air mixtures inside an engine, as explained above. The present invention overcomes this shortcoming. Furthermore, U.S. Pat. No. 6,762,835 does not use a "window" (as described herein), and since U.S. Pat. No. 6,762,835 is just used for molten material analysis, it does not face any challenges like window contamination during the measurement process that exist when monitoring diagnostic light from combustion.

Accordingly, there is a need for a system for generating a spark in an engine cylinder utilizing an optic fiber. In addition, there is a need for performing diagnostics on the spark and/or combustion flame within the cylinder.

SUMMARY OF THE INVENTION

The present invention is generally directed to solving these and other problems of the prior art. In accordance with embodiments of the present invention, a system for generating a spark is provided, including generating a spark in a combustion chamber of an internal combustion engine. Embodiments of the present invention provide for a laser beam that is launched into, and passed through, a hollow fiber. The beam exits the fiber and is demagnified (focused) using exit or downstream optics, thereby producing a spark. Embodiments of the present invention allow the spark to be moved away from the relatively cold spark plug electrodes and combustion chamber walls, thus removing two of the "heat sinks" that can slow down early flame growth in a conventional spark ignition engine and allowing the spark to be positioned at other locations which may provide other combustion benefits. The spark formation process is not initiated by high voltage, so the problems of dielectric breakdown and spark plug erosion are avoided. Indeed, spark creation with a laser becomes easier as cylinder pressure and density increase because at optical frequencies the required intensity to spark reduces with pressure, whereas the trend is opposite for conventional spark plugs since for conventional spark plugs the required electric field to spark increases with pressure.

Furthermore, by applying certain coatings to the inner wall of the hollow fiber the efficiency of light guiding can be increased, even in bent configurations. By doing so, the flexible coated hollow core fiber is able to deliver laser pulses to form sparks. In accordance with embodiments of the present invention, a system for generating a spark is provided, wherein the system comprises a laser beam and launch focusing optic or optics for receiving the laser beam, wherein the launch focusing optic or optics yield a focused beam of laser light at the entrance of the fiber. As used herein, both of the terms "optic" and "optics" refer to one or more devices for altering a beam of light, as for example, a single lens (simple or compound), a (curved) mirror, an active or adaptive optic, a diffractive optic, or a plurality of the aforementioned components.

In one embodiment of the invention, the launch focusing optics comprises at least one lens or curved mirror (or other appropriate optic). The system for generating a spark also includes a laser transmission fiber comprising a hollow bore and a wall surrounding the hollow bore (i.e., a hollow fiber), wherein the laser transmission fiber receives the focused beam of laser light at a fiber entrance. The laser transmission fiber transmits the beam of laser light through the fiber, and the beam of laser light exits the laser transmission fiber at a fiber exit as an exit beam of laser light. The system also includes exit focusing optics for receiving the exit beam of laser light from the fiber exit. In one embodiment of the invention, the exit focusing optics comprises at least one lens (or curved mirror or other appropriate optic), or alternatively, a plurality of lenses (or curved mirrors or other optic combinations). The exit focusing optics yields a focused beam capable of generating a spark.

In accordance with yet other embodiments of the present invention, a spark generating system is provided in combination with a combustion engine. In particular, the spark generation system is used to introduce a focused beam of laser light into a combustion chamber of the engine, thereby generating a spark within the combustion engine. In accordance with embodiments of the present invention, a multiplexer may be used with a single laser source and a plurality of hollow fibers for generating sparks at a plurality of spark targets, such as plurality of cylinders within a single combustion engine.

In accordance with embodiments of the present invention, sparking at the launch or at other locations within the fiber is at least partially alleviated by introducing (or flowing) a gas with high ionization potential (e.g., helium) or by using a vacuum set-up to lower the gas pressure at the launch and/or within the fiber. Both methods increase the breakdown threshold and thus help avoid sparking.

In accordance with other embodiments of the present invention, a method of generating a spark is provided. In general, the method involves using the spark generating system described above. More particularly, the method comprises providing a laser light source for generating a laser beam and providing launch optics for receiving the laser beam, wherein the launch optics yield a focused beam of laser light at the entrance of the fiber. The method also includes providing a laser transmission fiber comprising a hollow bore and a wall surrounding the hollow bore. The laser transmission fiber receives the focused beam of laser light at the fiber entrance. The laser transmission fiber transmits the focused beam of laser light through the fiber, and the beam of laser light exits the hollow fiber at a fiber exit as an exit beam. The method also includes aligning the launch lens with the fiber entrance of the laser transmission fiber. The method also includes providing exit optics in optical communication with the fiber exit, wherein the exit optics receives the exit beam of laser light from the fiber exit, and wherein the exit optics yields a focused beam for generating a spark. In addition, the method comprises generating a laser beam from the laser light source, wherein the laser beam generates the spark. The method may be used with a combustion engine, wherein the exit optics are operatively associated with a spark plug interconnected to a combustion engine.

In accordance with other embodiments of the present invention, a system of generating a spark is provided, wherein a fiber laser is utilized. The fiber laser provides a beam of laser light that exits the fiber laser at a fiber exit. The system also includes exit focusing optics for receiving the laser beam from the fiber laser. In one embodiment of the invention, the exit focusing optics comprises at least one lens (or curved mirror or other appropriate optic), or alternatively, a plurality of lenses (or curved mirrors or other optic combinations). In yet another alternative embodiment, the exit face of the optic fiber of the fiber laser may include an integral optic for focusing or assisting in focusing the laser beam that is being emitted from the optic fiber of the fiber laser. Such integral optic may limit or negate the need for separate exit focusing optics.

In accordance with embodiments of the present invention, the fiber laser yields a focused beam capable of generating a spark.

In accordance with other embodiments of the present invention, a method of generating a spark is provided, the method comprising providing a fiber laser for generating a laser beam through a fiber exit of the fiber laser, and generating the spark using exit optics in optical communication with the fiber exit, wherein the exit optics receives the laser beam from the fiber exit, and wherein the exit optics yields a focused beam for generating the spark. For such a method, the exit optics may be operatively associated with a spark plug interconnected to a combustion engine. In addition, the method may further comprise directing the laser beam to a plurality of spark targets using a multiplexer.

In accordance with other embodiments of the present invention, a spark and diagnostic system is provided, wherein the system can be used to provide information on light. Embodiments of the present invention include collecting the diagnostic light, where the diagnostic light may be light from the spark itself, or light from a flame resulting from the spark. As for example, for sparking performed within an engine cylinder, the diagnostic light collected from within the cylinder may include light from the spark and/or light from a combustion flame. In addition, embodiments of the present invention include providing a spark for diagnostic analysis of oil used in the engine. Embodiments of the present invention include using a multiplexer to provide laser light to more than one location, such as to more than one cylinder in an engine, and/or to one or more separate fluid locations, such as an oil testing chamber or other fluid testing location.

A variety of configurations for generating a spark and collecting diagnostic light are provided herein. At least one embodiment comprises using a laser source, launch optics and hollow fiber, together with focusing (or exit) optics for generating a spark within an engine cylinder. Diagnostic light from the spark and/or flame from within the cylinder is then relayed for analysis, where the means for relaying may comprise the hollow fiber. Alternatively, a separate optic fiber may be used for relaying the diagnostic light, or the diagnostic light may be relayed with other optics, such as one or more mirrors, that do not include an optic fiber. In yet another embodiment of the present invention, a fiber laser is used, potentially together with focusing (or exit) optics, for generating a spark within an engine cylinder. Diagnostic light from the spark and/or flame from within the cylinder is then relayed for analysis. In accordance with embodiments of the present invention, components of a spark generating and diagnostic system may further include a dispersive element and/or a photodetector. In addition, other optics may be used, such as a dichroic mirror.

Additional aspects, embodiments and details of embodiments of the present invention are described herein. As such, various embodiments of the present invention are set forth in the attached figures and in the detailed description of the invention as provided herein and as embodied by the claims. It should be understood, however, that this Summary of the Invention may not contain all of the aspects and embodiments of the present invention, is not meant to be limiting or restrictive in any manner, and that the invention as disclosed herein is and will be understood by those of ordinary skill in the art to encompass obvious improvements and modifications thereto.

Additional advantages of the present invention will become readily apparent from the following discussion, particularly when taken together with the accompanying drawings.

BRIEF DESCRIPTION OF THE DRAWINGS

FIG. 3 is a side elevation view of the launch assembly in accordance with embodiments of the present invention;

FIG. 4 is a perspective view of a laser transmission fiber in accordance with embodiments of the present invention;

FIG. 5 is cross-sectional view of the laser transmission fiber of FIG. 4 taken along line 5-5 of FIG. 4;

FIG. 11A is a side elevation view of the fiber laser exit and exit focusing optics in accordance with embodiments of the present invention;

FIG. 11B is a side elevation view of the fiber laser exit with an end cap and with an integral focusing lens in accordance with embodiments of the present invention;

The drawings are not necessarily to scale.

DETAILED DESCRIPTION OF THE INVENTION

Figure 1:
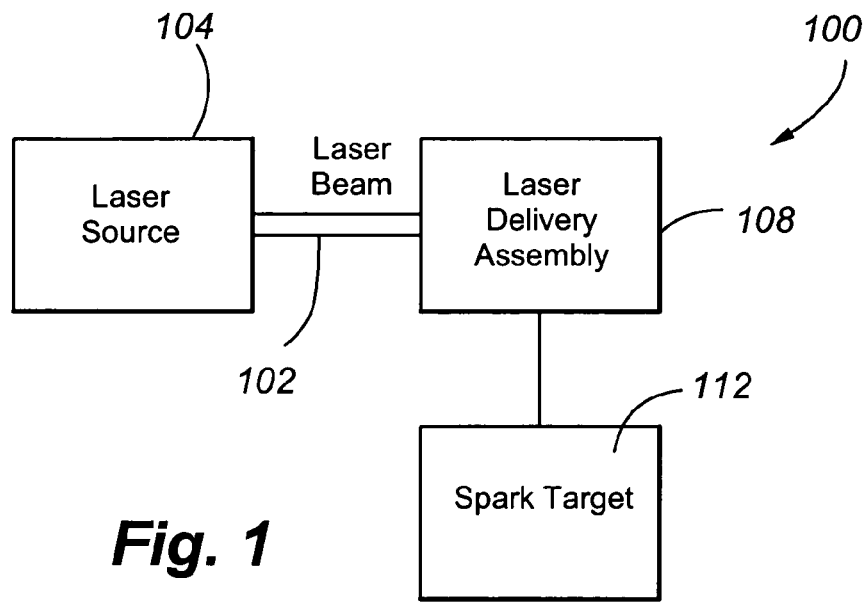
FIG. 1 is block diagram depicting components of a system in accordance with embodiments of the present invention.

FIG. 1 illustrates a spark delivery system 100 in accordance with embodiments of the present invention. The system 100 generally includes a laser source 104 in optical communication with a laser delivery assembly 108, which in turn is in optical communication with a spark target 112. The laser source 104 provides a beam of laser light 102 to the laser delivery assembly 108. In order to provide a desirable launch, a laser source 104 with a relatively high spatial quality is desirable. It is estimated that a laser source 104 with a spatial quality $M^2$ parameter of less than about 10 is required. In accordance with embodiments of the present invention, and by way of example and not limitation, a laser source 104 such as a Continuum 8050 Nd:YAG laser has been found to provide an acceptable laser beam 102 for sparking. In accordance with embodiments of the present invention, and by way of example and not limitation, a wavelength of 1064 nm has been found sufficient for sparking; however, many wavelengths of light are anticipated to work and are within the scope of the present invention. The laser delivery assembly 108 manipulates and conveys the laser light beam to the spark target 112. The spark target 112 can be a variety of devices or structures, such as, but not limited to, a combustion engine or another device requiring an ignition source. For the case of a combustion engine, the spark is formed within the gaseous region inside the combustion chamber or engine cylinder.

Figure 2:
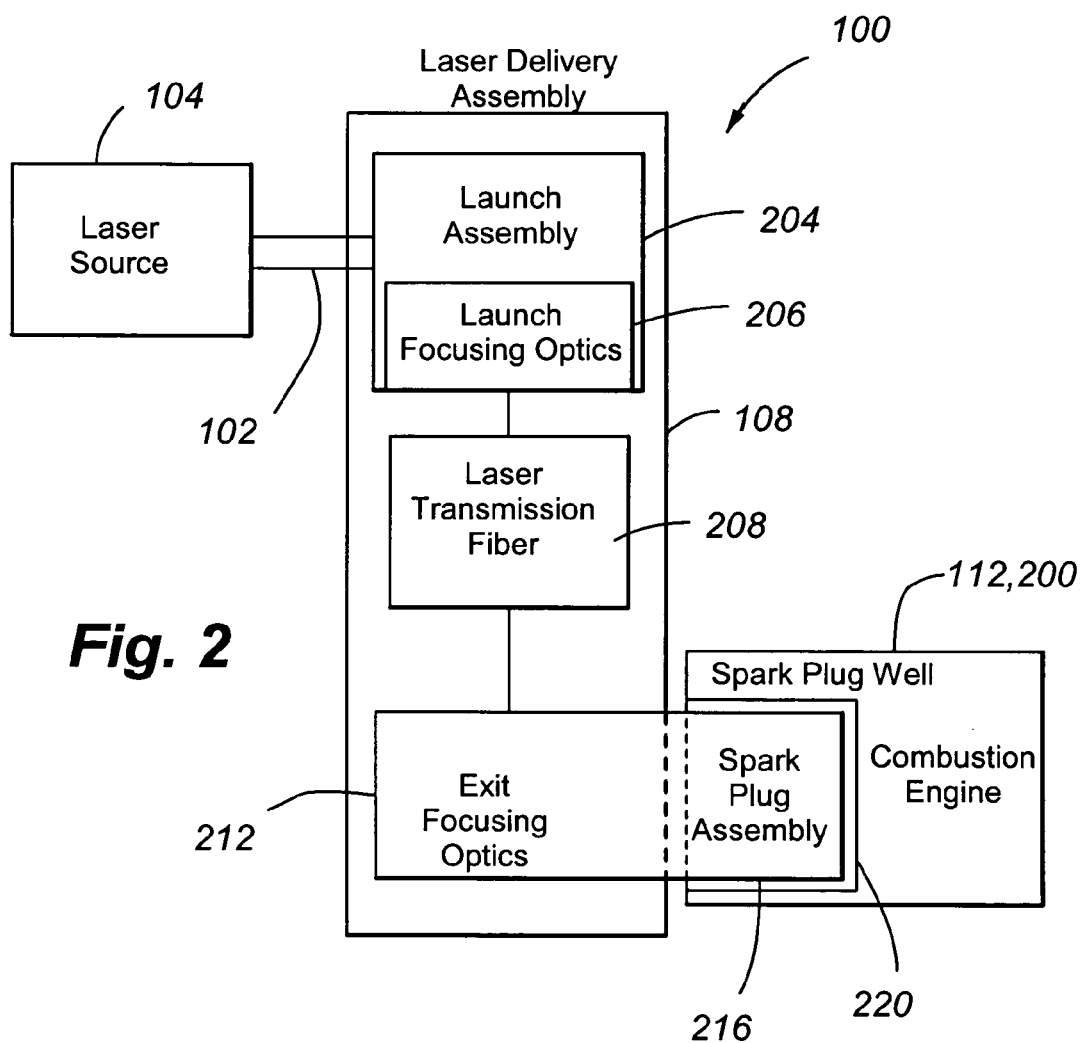
FIG. 2 is a block diagram depicting a combustion engine used in accordance with embodiments of the present invention.

Referring now to FIG. 2, a spark delivery system 100 is illustrated in accordance with an embodiment of the present invention, wherein the system 100 includes a spark target 112 comprising a combustion engine 200. FIG. 2 further illustrates that the laser delivery assembly 108 includes a launch assembly 204 that comprises launch focusing optics 206. In addition, the laser delivery assembly 108 includes a laser transmission fiber 208, and exit focusing optics 212. The exit focusing optics 212 are in optical communication with an optical spark plug assembly 216, which is interconnected to the combustion engine 200. By way of example and not limitation, the spark plug assembly 216 may contain at least a portion of the exit focusing optics. In addition, at least a portion of the spark plug assembly 216 may be inserted into a spark plug well 220 of the combustion engine 200.

Referring now to FIG. 3, in accordance with embodiments of the present invention, aspects of the launch assembly 204 are illustrated. The launch assembly 204 includes launch focusing optics 206 that receive the laser beam 102 generated by the laser source 104. In accordance with embodiments of the present invention, and by way of example and not limitation, as shown in FIG. 3, the launch focusing optics 206 may comprise a single launch lens 304, such as a plano-convex lens of 50 cm focal length; however, other lenses (simple or compound) and focal lengths other optics (such as (curved) mirrors, as well as diffractive optics and active or adaptive optics, and/or other appropriate optics) are within the scope of the present invention. Moreover, it can be appreciated and is to be understood that the launch focusing optics 206 (and exit optics as described below) may alternatively comprise a plurality of optical components, such as lenses, (curved) mirrors, diffractive optics, active or adaptive optics, and other appropriate optics and combinations of the aforementioned, etc. Indeed, it is anticipated that a variety of possible types of lens or lens systems are appropriate for use in the present invention, where the lens or lens systems may differ in material, shape and number. Thus, the focusing optics and exit optics may comprise mirrors and/or other devices different than a lens or lens system. In addition, the use of adaptive optics is disclosed in U.S. Pat. No. 6,796,278, which is incorporated herein by reference in its entirety. The use of all of such available devices are within the scope of the present invention.

In accordance with embodiments of the present invention, the focusing optics 206 or launch lens 304 demagnifies and focuses the light to launch the laser beam 102 into the laser transmission fiber 208. However, it is to be understood that alternate embodiments may comprise magnification optics depending upon the size of the laser beam diameter and the size of the fiber. By way of example and without limitation, for a launch using a single lens and a relatively collimated laser beam, the distance between the launch lens 304 and the fiber entrance 308 of the laser transmission fiber 208 is approximately the lens focal length $f_{launch}$. The launch lens 304 receives a laser beam 102 entering the launch lens 304 in the direction of arrow $A_1$. By way of example and not limitation, in an embodiment of the present invention the laser beam 102 has a beam diameter $d_{beam}$ of about 1 cm. By way of example and not limitation, in an embodiment of the present invention, the launch lens 304 demagnifies and focuses the laser beam 102 with a focal length $f_{launch}$ of about 50 cm as it enters the laser transmission fiber 208 in the direction of arrow $A_2$. For these conditions, the launch angle $\theta_{launch}$ of the focused laser light 306 is about 0.01 radians, yielding an exit angle $\theta_{exit}$ of light of approximately 0.01 to 0.02 radians. More generally, the launch angle should preferably be less than about 0.03 radians, and more preferably, less than about 0.015 radians, and the light exiting the fiber should have an exit angle $\theta_{exit}$ of less than about 0.03 radians, and more preferably, less than about 0.015 radians exiting the laser transmission fiber 208 near the exit focusing optics 212 (see FIG. 6), where both the launch angle $\theta_{launch}$ and the exit angle $\theta_{exit}$ of light represent the angles of the light rays having the widest angle with respect to the optical center axis at the respective component.

Referring now to FIGS. 3 and 4, a laser transmission fiber 208 in accordance with an embodiment of the present invention is illustrated. The laser transmission fiber 208 comprises an optic fiber having a hollow bore 400 and a wall 404 circumscribing and surrounding the hollow bore 400. The wall 404 surrounding the hollow bore 400 has an interior wall surface 408. In addition, the wall 404 comprises an exterior wall surface 412. In order to be practically useful, the laser transmission fiber is preferably flexible, with a variety of possible radii of curvature. More particularly, a flexible fiber is preferred, and it is anticipated that a fiber having a radius of curvature of greater than at least about 1 to 10 cm is functional; that is, a variety of curvatures are possible from nearly straight fibers with an infinite or nearly infinite radius of curvature, to fibers having a radius of curvature as low as about 1 to 10 cm.

As noted above, in one embodiment of the present invention the laser beam 102 entering the launch lens 304 has a beam diameter $d_{beam}$ of about 1 cm. As the launch angle $\theta_{launch}$ is decreased, the diameter of the beam at the fiber entrance 308 increases. However, it is necessary for the diameter of the beam $d_{beam\ entrance}$ at the fiber entrance 308 to be less than the diameter $d_{fiber\ hollow\ diameter\ at\ entrance}$ of the hollow bore of the fiber 208 at the fiber entrance 308 in order to prevent sparking at the fiber face (which may occur if the edge of the beam overlaps the fiber wall), and to transfer sufficient beam energy to the fiber 208. As will be appreciated by those skilled in the art, the beam intensity of a laser beam is generally not uniform. Thus, there are different ways to define the beam diameter. As used herein, the beam diameter is twice the mathematical variance of the intensity profile. That is, the diameter of the beam means the geometric diameter in the case of a uniform "top-hat profile" beam, or four times the variance (twice the waist) in the case of a beam with a non-spatially-uniform intensity profile.

In addition, if the diameter of the beam $d_{beam\ entrance}$ at the fiber entrance 308 becomes too small, the corresponding intensity will become sufficiently high to cause sparking of the ambient gas at the fiber entrance 308. Accordingly, the diameter of the beam $d_{beam\ entrance}$ at the fiber entrance 308 should be not so small that the intensity at the fiber entrance reaches the breakdown intensity and causes a spark at the fiber entrance. In practice, this will generally, but not necessarily, require a diameter between about 10 and 90% of the outside diameter $d_{fiber\ hollow\ diameter\ at\ entrance}$ of the fiber 208 at the fiber entrance 308. By way of example and not limitation, in one embodiment of the invention, the diameter of the beam $d_{beam\ entrance}$ at the fiber entrance 308 is about 300 microns for a fiber 208 having a diameter $d_{fiber\ hollow\ diameter\ at\ entrance}$ of about 700 microns at the fiber entrance 308.

In accordance with embodiments of the present invention, five axes of control are needed to correctly align the fiber 208 with the focused laser light 306, assuming that the light beam is fixed, and that the fiber is aligned with the beam. The axes comprise the three spatial axes (i.e., the position of the fiber input) as well as two tilt axes. Spatially, the x axis is the least critical, requiring placement of the fiber entrance within a few millimeters of the launch beam waist along the beam's axial direction. However, both the spatial y and z axes and the two tilt axes must be carefully aligned (on the order of 10's of microns and milli radians for the example parameter values given above) to get efficient transmission through the fiber and to avoid exciting higher order modes and thereby further decreasing the spatial quality (increasing $M^2$) of the beam through the fiber 208. It is also noted that it would be possible to perform a combination of aligning the beam to the fiber and the fiber to the beam, in which case less than five axes would be needed for the beam adjustment since one or more axes could be done with laser adjustment.

Referring now to FIG. 5, a cross section of a transmission fiber in accordance with at least one embodiment of the invention is shown. The interior wall surface 408 is coated with an interior coating 500, and the exterior wall surface 412 is coated with an exterior coating 504. The coating 500 may be formed of a single or multiple number of layers, or may be integral to the wall material. The coating 504 may be formed of a single or multiple number of layers. Alternatively, in one embodiment, the exterior coating 504 may be absent. In addition, the coatings may be formed from metal and/or other materials (e.g., polymers). Typically, the layer thicknesses must be tightly controlled, generally as a function of the laser wavelength, to allow for effective light guiding. By way of example and not limitation, in one embodiment of the invention, the coating 500 is comprised of a layer of silver of approximately 0.2 microns in thickness, which is on the inner wall surface 408, and a cyclic olefin polymer coating (placed on the silver coating) of approximately 0.1 microns in thicknesses.

Figure 6:
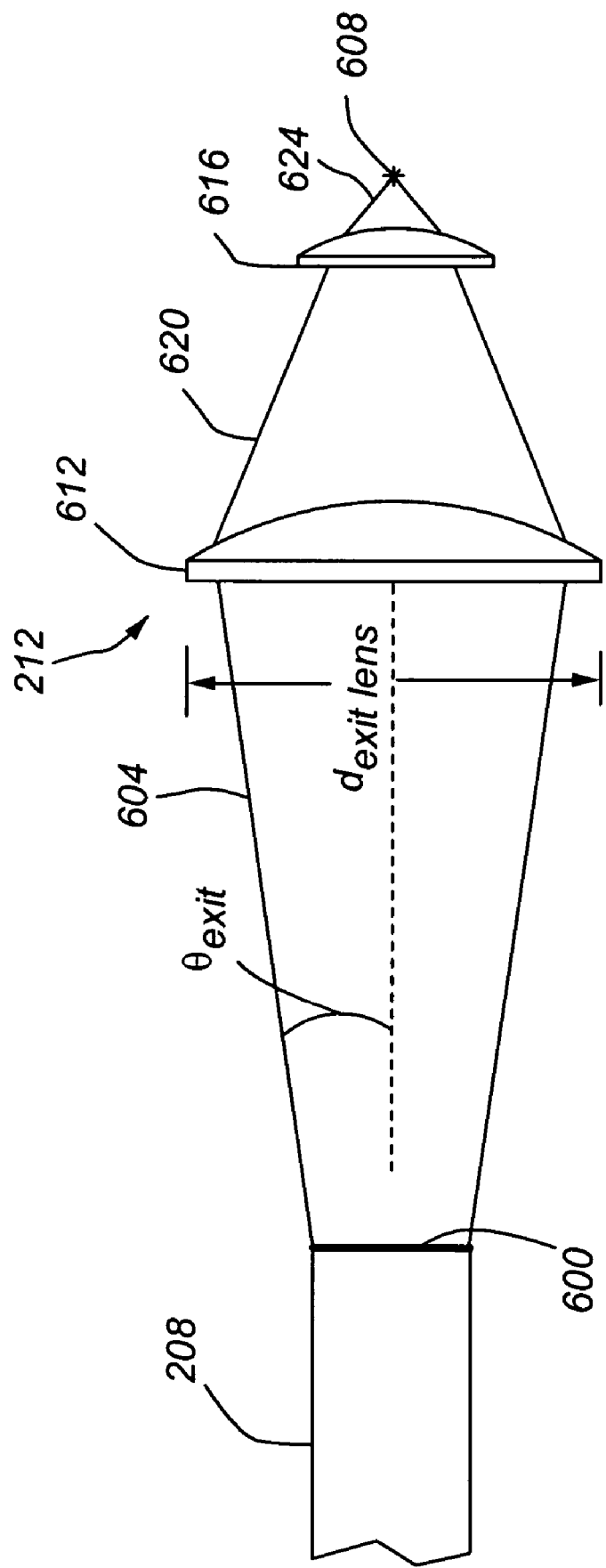
FIG. 6 is a side elevation view of the fiber exit and exit focusing optics in accordance with embodiments of the present invention.

Referring now to FIG. 6, in accordance with embodiments of the present invention, the fiber exit 600 and exit focusing optics 212 are shown. Light traveling through the fiber 208 exits the fiber at an exit angle $\theta_{exit}$ at the fiber exit 600. The exit beam 604 is directed toward the exit focusing optics 212, in which the beam 604 is demagnified to create a spark 608.

In accordance with embodiments of the present invention, the exit focusing optics 212 are selected to allow small focal spots at the desired spark location, thus providing high demagnification of light exiting the fiber, and thereby providing high intensities at the desired spark location. Since the exit beam 604 exiting the fiber 208 is not collimated, the separation distance of the exit focusing optics 212 from the fiber exit 600 is important. An effective configuration comprises a low f# ("f number") optic system; that is, a low ratio of effective focal length to lens fill diameter, and is positioned downstream from the fiber exit 600 in such a way that the exit beam 604 does not exceed the exit lens diameter $d_{exit\ lens}$ (i.e., the beam should not overfill the lens). A low f# system is required as it is capable of focusing the light leaving the fiber to a small beam diameter to achieve the required high intensity. As shown in FIG. 6, and by way of example and without limitation, at least one embodiment of the present invention employs two exit lenses 612 and 616 with a resulting demagnification ratio of the light dimension leaving the fiber to the light dimension at the spot of the spark 608 of about 10. The exit lenses 612 and 616 demagnify the exit beam 604 to create focused beams 620 and 624, thereby providing the intensity required to produce the spark 608.

The practical limitation on low f# optics which give high demagnification, is that aberrations tend to become increasingly prevalent as the f# is reduced. Since aberrations cause larger spot sizes and thus are undesirable because they decrease the intensity of the beam at the spark location, an imaging system with simultaneous low f# and low aberrations is preferable. In accordance with embodiments of the present invention, the exit focusing optics 212 allow appropriate demagnification and refocusing. By way of example and without limitation, the exit focusing optics 212 may be based on a single- or multi-lens system, and may use simple spherical lenses, plano-spherical lenses, achromatic lenses, or aspheric lenses. Alternatively, the exit optics 212 may comprise other optics, either with or without the use of one or more lenses, such as one or more curved mirrors, and/or adaptive optics, allowing appropriate demagnification and refocusing.

The exit focusing optics 212 allow the spark 608 to be positioned at a desired location. For example, when used in a combustion engine 200, the exit optics 212 may be designed to provide demagnification of the exit beam 604 such that the spark 608 is generated at an optimum location. More particularly, by adjusting the exit optics 212, the spark 608 may be moved away from the relatively cold combustion chamber walls, thus removing the walls as a "heat sink" that can slow down early flame growth in an engine. As discussed earlier, there may be other benefits associated with moving the spark location.

In accordance with other embodiments of the invention, a method of generating a spark using a spark delivery system 100 as described herein is provided. In use, a laser source 104 is provided and a laser beam 102 is directed to a laser delivery assembly 108. The laser beam 102 is received by launch focusing optics 206 that typically comprises at least one launch lens 304, but may be comprised of other devices, such as a mirror. The focused laser light 306 from the launch lens 304 is directed to a fiber entrance 308 of a laser transmission fiber 208 that comprises a coated hollow core fiber that is preferably flexible. The process of directing the laser light 306 from the launch lens 304 to the fiber entrance 308 typically entails aligning the light 306 along five axes of control, including three spatial axes and two tilt axes. After the light passes through the fiber 208 and exits the fiber 208 at a second end or fiber exit 600 of the fiber 208, the exit beam 604 is then directed to exit focusing optics 212 which may comprise one or more lenses, such as exit lenses 612 and 616. The exit focusing optics 212 cause an increase in intensity of the exit beam 604, creating an electrical breakdown at the location of the spark target 112, thereby creating a spark 608. For use in a combustion engine 200, the exit focusing optics 212 are interconnected to a spark plug assembly 216 that is interconnected to the combustion engine 200, such as through a spark plug well 220. When the spark 608 is created in an ignitable gas, the spark causes ignition within the engine 200.

Figure 8:
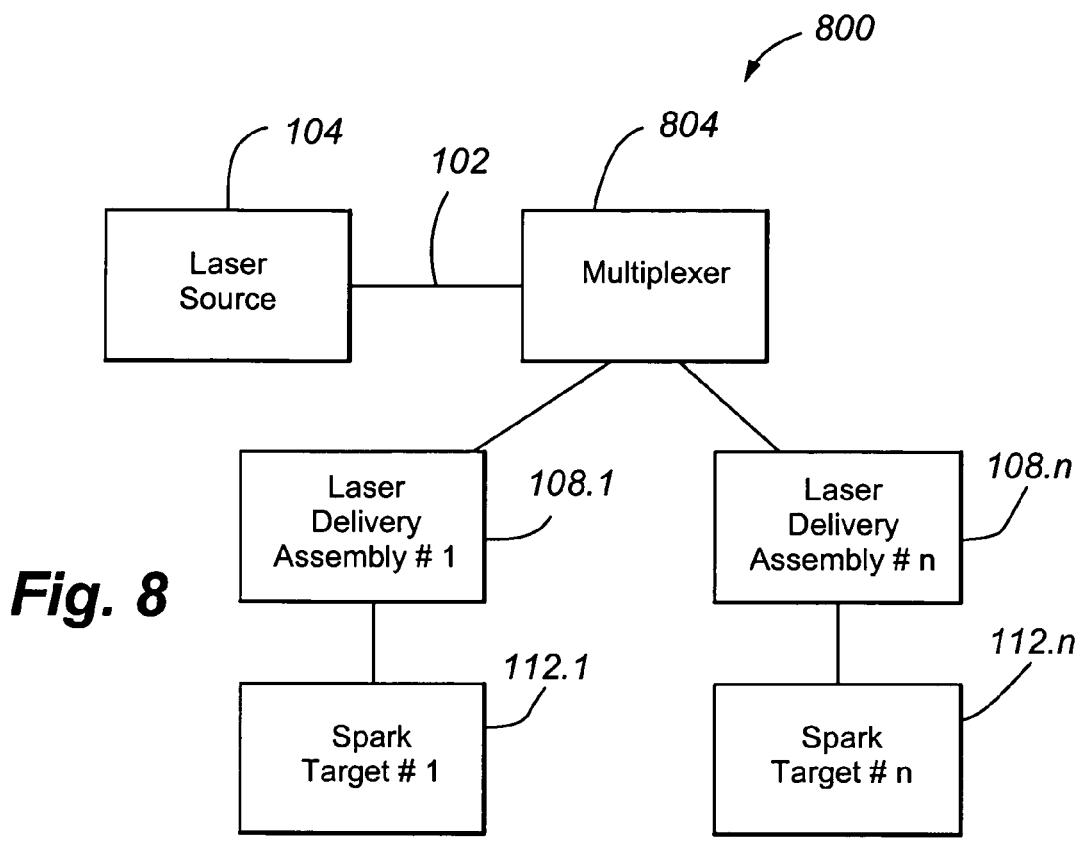
FIG. 8 is a block diagram depicting a multiplexed spark delivery system in accordance with embodiments of the present invention.

Referring now to FIG. 8, in accordance with embodiments of the present invention, a multiplexed spark delivery system 800 can be used, wherein a single laser source is used to provide a laser beam to a plurality of hollow fibers. As shown in FIG. 8, a multiplexer 804 is positioned between the laser source 104 and a plurality of laser delivery assemblies 108.1-108.n, wherein the laser delivery assemblies 108.1-108.n deliver a focused laser beam to spark targets 112.1-112.n, respectively. By way of example and without limitation, a multiplexed spark delivery system 800 can be used with a combustion engine, wherein a single laser source is used to provide a laser beam through a plurality of hollow fibers leading to multiple cylinders within a single combustion engine.

In a separate embodiment of the invention, a method of choosing a fiber for creating an optical spark is provided. The method involves calculating a figure of merit ("FOM") to compare the different types of fibers, as well as fiber lasers, in terms of their effectiveness for creating optical sparks. The figure of merit was derived from the point of view of paraxial ray-tracing (geometric optics), and may also be derived from spatial beam quality ($M^2$) considerations. Both analyses are equivalent under certain simplifying assumptions, namely, that the light exiting the fiber has a waist (minimum spot-size) equal to the fiber radius and that the far-field beam divergence matches the fiber exit angle.

Figure 7:
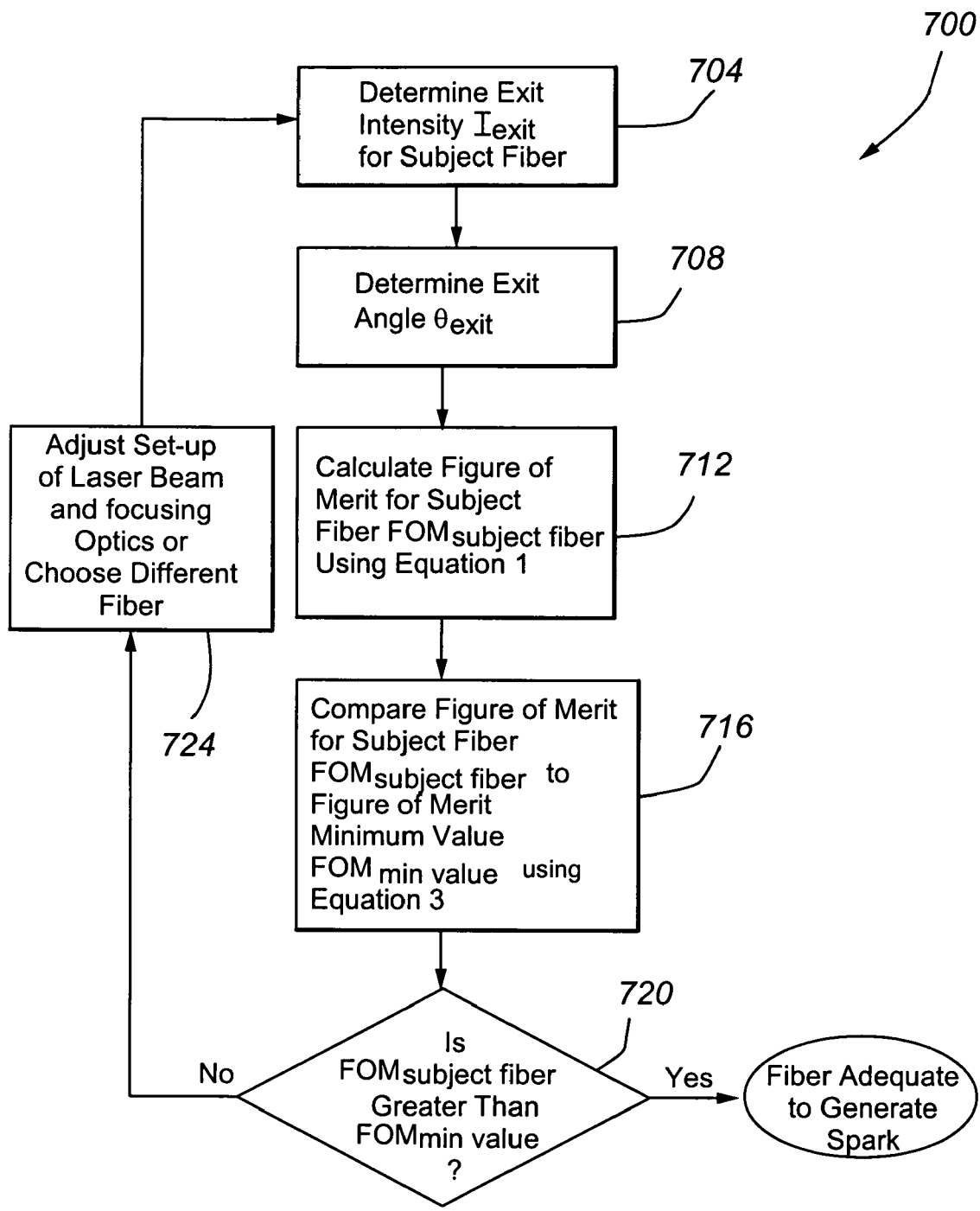
FIG. 7 is a flow diagram depicting aspects of a method of choosing a fiber to create a spark using a laser in accordance with embodiments of the present invention.

With reference now to FIG. 7, a method of choosing a fiber for creating an optical spark in accordance with an embodiment of the present invention is illustrated in a flow diagram. The method applies to a single lens and a multi-lens imaging system. The method of choosing a fiber includes calculating a figure of merit "FOM" for the subject fiber $FOM_{subject\ fiber}$, and comparing this value to a calculated figure of merit minimum value $FOM_{min\ value}$ for creating a spark. For ease of analysis, it is assumed that the light at the fiber exit uniformly fills the fiber diameter, and that the final focusing optics have negligible transmission loss. More specifically, the intensity should be considered as the spatially and temporally averaged intensity.

The figure of merit for the subject fiber:

$$FOM_{subject\ fiber} = \frac{I_{exit}}{\theta_{exit}^2} \qquad \text{[Equation 1]}$$

and intensity at the spark location is given as:

$$I_{spark} = \frac{I_{exit}\ \theta_{spark}^2}{\theta_{exit}^2} \qquad \text{[Equation 1.5]}$$

Thus, the figure of merit minimum value for creating a spark is given as:

$$FOM_{min\ value} = \frac{I_{spark}}{\theta_{spark}^2} \qquad \text{[Equation 2]}$$

where $I_{spark}$ is the minimum intensity value required to create a spark.

For these equations, the figure of merit is independent of the focusing optics. Assuming the required intensity at the spark location is $2\pm1\times10^{11}$ W/cm$^2$, and that the best achievable imaging is $\theta_{spark}$=0.38±0.13 radians (which corresponds to 0.5 to 0.25 radians, or equivalently a minimum imaging f#=1 to 2, then the minimum value FOM$_{min\ value}$ for creating a spark is:

$$FOM_{min\ values} \geq 1400 \pm 800\ GW/cm^2/rad^2 \quad \text{[Equation 3]}$$

The uncertainty in the FOM$_{min}$ is due to uncertainty in both the required intensity to spark ($I_{spark}$), and in the maximum possible divergence angle ($\theta_{spark}$) at the spark location, corresponding to minimum possible imaging f#. For example, if higher intensities are required to spark, the FOM$_{min}$ will increase as given by Equation 2, and the same logic applies to variation in $\theta_{spark}$.

The figure of merit for the subject fiber FOM$_{subject\ fiber}$ clearly shows that to achieve a high intensity at the intended spark location requires a high intensity ($I_{exit}$) at the fiber exit, as well as a low divergence angle or exit angle $\theta_{exit}$ at the fiber exit. This method may be used to compare the ease with which different sources (i.e. fiber types) can be focused to high intensity to produce sparks.

By way of example, a comparison is provided in Table 1 to compare different sources, and to gage the effectiveness of a given source for creating sparks, the FOM may be evaluated for different available solid and hollow core fiber optics. Results are given in Table 1 below. In Table 1, solid fiber refers to standard (commercial) silica step-index fibers of numerical aperture (NA) of 0.11.

TABLE 1

| Source | $I_{exit}$ (GW/cm$^2$) | $\theta_{exit}$ (Rad) | FOM$_{subject\ fiber}$ [Equation 1] (GW/cm$^2$/rad$^2$) |
|---|---|---|---|
| Solid Fiber (base NA) | ~3 | ~0.11 | ~250 |
| Solid Fiber (lower NA) | ~3 | ~0.05 | ~1200 |
| Coated Hollow Fiber | ~2 | ~0.015 | ~8900 |
| Fiber Laser | ~5 | ~0.015 | ~22,200 |

With regard to the data presented in Table 1, the exit intensities $I_{exit}$ for the fibers are believed to be the highest reported for nanosecond lasers. Solid fibers are generally characterized by their Numerical Aperture (NA) which is defined by fiber index of refraction and generally corresponds also to the exit angle $\theta_{exit}$. The exit angles $\theta_{exit}$ for the Solid Fiber (base NA) is defined by an NA=0.11, which is typical for solid fibers. (Lower NA fibers are available in some cases but are generally less robust). Using the present method, the figure of merit for the subject fiber FOM$_{subject\ fiber}$ yields a value of approximately 250 GW/cm$^2$/rad$^2$ for the Solid Fiber (operated at base NA). This value is significantly lower than the minimum value FOM$_{min\ value}$ for creating a spark. Therefore, the present method rules out use of the Solid Fiber (base NA) for creating a spark.

The second row of Table 1 presents values for a solid fiber that operates with a lower exit angle (NA), which can be achieved by modifying the light delivery at the fiber entrance. The exit angle $\theta_{exit}$ value of 0.05 radians corresponds approximately to half the standard NA. Again, using the present method, the figure of merit for the subject fiber FOM$_{subject\ fiber}$ yields a value of approximately 1200 GW/cm$^2$/rad$^2$ for the Solid Fiber (lower NA). This value is in the range of the range for the minimum value FOM$_{min\ value}$ for creating a spark. Therefore, the present method indicates that use of the Solid Fiber (lower NA) may be possible for creating a spark. However, when operating at lower than base NA, the possible exit intensity tends to decrease, which causes a lowering of the FOM$_{subject\ fiber}$ for such implementations.

For the coated hollow fiber, the exit angle $\theta_{exit}$ value of 0.015 radians and the values of exit intensity are based on inferences from reported work and experiments. Using the present method, the figure of merit for the subject fiber FOM$_{subject\ fiber}$ yields a value of approximately 8900 GW/cm$^2$/rad$^2$ for the Coated Hollow Fiber. This value is greater than the range for the minimum value FOM$_{min\ value}$ for creating a spark. Therefore, the present method indicates that use of a Coated Hollow Fiber is acceptable for creating a spark.

For fiber lasers, the intensity and exit angle parameter values vary. Possible values are given in row 4 of Table 1, and correspond to a Figure of Merit greater than the range for the minimum value FOM$_{min\ value}$ for creating a spark. Therefore, a fiber laser with these parameters can readily produce a spark.

With Reference again to FIG. 7, a method of choosing a laser transmission fiber 700 is provided. As shown in box 704, the method of choosing a fiber comprises determining the exit intensity $I_{exit}$ for a subject fiber. As shown in box 708, the method also includes determining the exit angle $\theta_{exit}$ of the widest rays of light exiting the subject fiber. In addition, as shown in box 712 the method includes calculating the figure of merit for the subject fiber FOM$_{subject\ fiber}$ using Equation 1. As shown in box 716, the method includes comparing the figure of merit for the subject fiber FOM$_{subject\ fiber}$ against the figure of merit minimum value FOM$_{min\ value}$ for creating a spark using Equation 3. As shown in box 720, if the calculated value for the figure of merit for the subject fiber FOM$_{subject\ fiber}$ of Equation 1 is less than the figure of merit minimum value FOM$_{min\ value}$ for creating a spark shown in Equation 3, the user of the method may attempt to adjust the launch conditions as shown in box 724. For example, the user can attempt to decrease the launch angle $\theta_{launch}$, thereby decreasing the exit angle $\theta_{exit}$, though associated changes in $I_{exit}$ must also be accounted for. Alternatively, the user may modify other conditions, such as the power of the laser beam in order to attempt to reach the minimum value FOM$_{min\ value}$ for creating a spark. If these modifications do not provide parameters yielding a sufficient figure of merit FOM$_{subject\ fiber}$ for the subject fiber, then the user can try a different type of fiber and repeat the process.

In a separate embodiment of the present invention, a system for generating a spark is provided, wherein the system utilizes a fiber laser. Fiber lasers overcome problems associated with intensity limits and launching the input light that are often associated with other fibers. Fiber lasers are capable of delivering high-quality and high-intensity laser pulses. In addition, because the fiber laser inherently consists of a fiber, the light exits from the fiber. The result is a source that does not require additional fiber coupling, and which has parameters that allow spark ignition.

In general, a fiber laser consists of a (solid) inner core typically of diameter 20 to 50 µm that is doped with a rare earth material, typically Ytterbium (Yb), Erbium (Er), or Thulium (TM). The doped core acts as the "gain medium", i.e. it is the medium in which a population-inversion is created and where lasing action (light amplification) occurs. In order to attain light amplification, the core needs to be "pumped" by a light source. The core is pumped by injecting the pump light into the fiber cladding (i.e., the fiber volume that surrounds the core). As with other solid fibers, the index of refraction of the core exceeds that of the cladding, so that there is total-internal-reflection of the light at the core/cladding interface, which is the mechanism by which the (core) light is transmitted through the fiber. In accordance with embodiments of the present invention, and by way of example and not limitation, the pump light may be supplied from a diode laser source, and may for example, have a wavelength of about 975 nm. Depending on the configuration, the pump light may be pulsed or continuous. The temporal output of the fiber laser may be determined by the pump light and/or by a Q-switch. An outer cladding may also be used to prevent the pump-light from leaking out of the main inner cladding.

In general, fiber lasers are long (typically tens of meters) and coiled so as to suppress the formation of higher modes. The mode suppression means that the laser output consists primarily of low order modes (low $M^2$ value). Such light can be focused to small dimensions (compared to high order modes), yielding the relatively high required intensities allowing spark formation. (See earlier $M^2$ discussion in the Background section). The output of a fiber laser can have $M^2$ less than about 1.3, which is significantly lower than the output of a conventional fiber of the same diameter.

The operating wavelength of the fiber laser is roughly determined by the gain profile of the gain (doped) material. The wavelength can be more precisely controlled through the use of an external seed laser that is a relatively low power laser beam that is injected into the fiber core and provides photons that cause the fiber laser to preferentially operate at the wavelength of the seed laser. In accordance with embodiments of the present invention, and by way of example and not limitation, a 1064 nm ND:YAG laser beam may be used as the seed laser. Also by way of example and not limitation, the fiber laser may provide a pulse energy of about 1 to 20 mJ, with a pulse duration of about 1 to 10 ns. In addition, the $M^2$ is less than about 1.5, with a fiber (core) diameter of about 20 to 50 microns. These parameters would allow both spark formation, and subsequent engine ignition for typical engine operating parameters. It is to be understood that other parameter values for a fiber laser other than foregoing values are also expected to allow spark formation and engine ignition for typical engine operating parameters.

Figure 9:
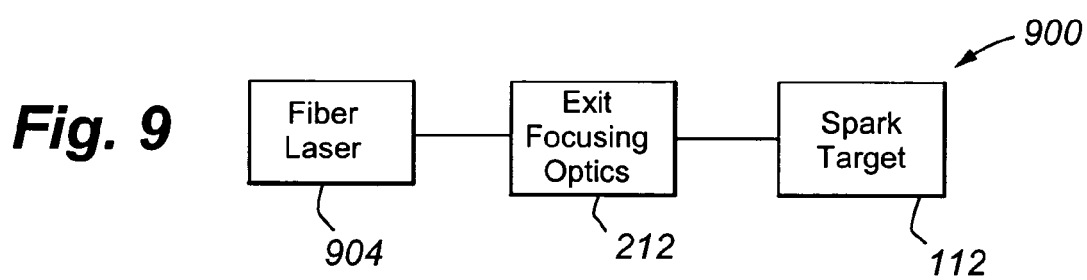
FIG. 9 is a block diagram depicting components of a system in accordance with embodiments of the present invention.

Referring now to FIG. 9, a spark delivery system 900 in accordance with embodiments of the present invention is illustrated. The system 900 generally includes a fiber laser 904 in optical communication with exit focusing optics 212, that in turn is in optical communication with a spark target 112.

Figure 10:
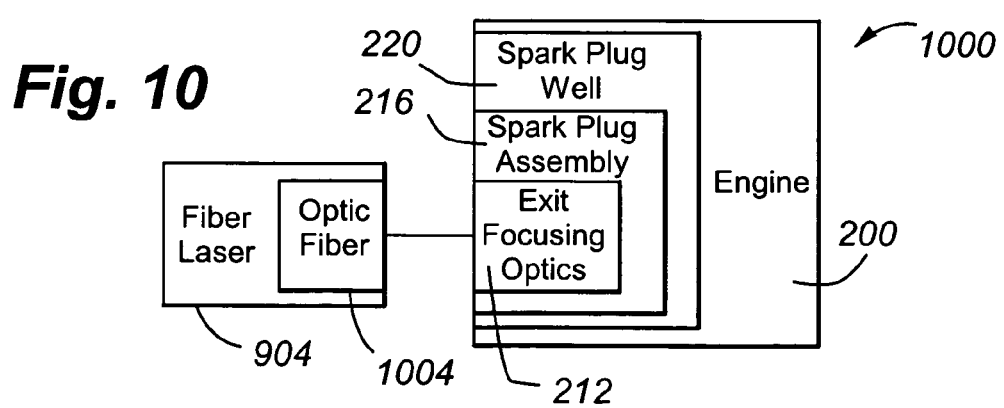
FIG. 10 is a block diagram depicting a combustion engine used in accordance with embodiments of the present invention.

Referring now to FIG. 10, and in accordance with embodiments of the present invention, a spark delivery system 1000 is shown that generates a spark in an engine, such as in a cylinder of a combustion engine. More particularly, the system 1000 comprises a fiber laser 904 that includes optic fiber 1004. The optic fiber 1004 of fiber laser 904 is in optical communication with exit focusing optics 212 that may reside in a an optical spark plug assembly 216. The optical spark plug assembly 216 is preferably fitted within a spark plug well 220 of a combustion engine 200.

Referring now to FIG. 11A, the optic fiber 1004 of the fiber laser 904 is shown in the vicinity of the exit focusing optics 212, where the exit focusing optics are similar to those described above for use with a laser transmission fiber having a hollow bore. Laser light emitted from the fiber laser 904 is focused to generate spark 608.

Referring now to FIG. 11B, in accordance with embodiments of the present invention, damage at the face of the fiber exit 600 may be avoided through the use of an end cap 1100. The end cap 1100 is a larger diameter piece of the same or similar material that the core of the optic fiber 1004 is made of. The end cap 1100 is preferably fused to the core fiber. As a high intensity laser beam emerges out of the fiber 1004 of fiber laser 904, the beam expands within the end cap 1100 so that the light is at a sufficiently lower level intensity than the damage threshold of the fiber 1004. The end cap 1100 does not significantly degrade the beam-quality ($M^2$) and does not limit the sparking potential.

Referring still to FIG. 11B, and in accordance with embodiments of the present invention, the exit surface of the fiber laser 904 may be curved so that it acts as an integral focusing lens 1104. In this way, the need for exit focusing optics typically located beyond the fiber exit 600 may be limited or negated, thereby providing the advantages of fewer surfaces to possibly damage, less hardware, and less optical loss.

In accordance with embodiments of the present invention, multiplexing of fiber lasers can be used to ignite multiple cylinders of an engine. In general, with multiplexing performed in conjunction with a fiber laser, each cylinder would have its own fiber laser output similar to the multiplexed hollow fibers shown in FIG. 8 and described above.

The laser spark delivery systems of the present invention may have applications in other areas, as for example, in medical or dental applications. Accordingly, the present invention disclosure encompasses the use of optical spark delivery in any appropriate application, not just for ignition.

In a separate embodiment of the present invention, a system for providing diagnostics of a light source is provided. In general, the use of laser ignition puts the inside of the engine cylinder in optical communication with the external environment. This then provides optical access to the engine cylinder, and such optical access provides not only a pathway for delivering laser light to generate a spark within the engine cylinder, but also provides an optical pathway for the collection of light generated within the cylinder, including the combustion (or flame) light, as well as the light from the spark itself. Thus, the optical communication path to the cylinder provides an opportunity for combined spark and diagnostics systems.

Figure 12A:
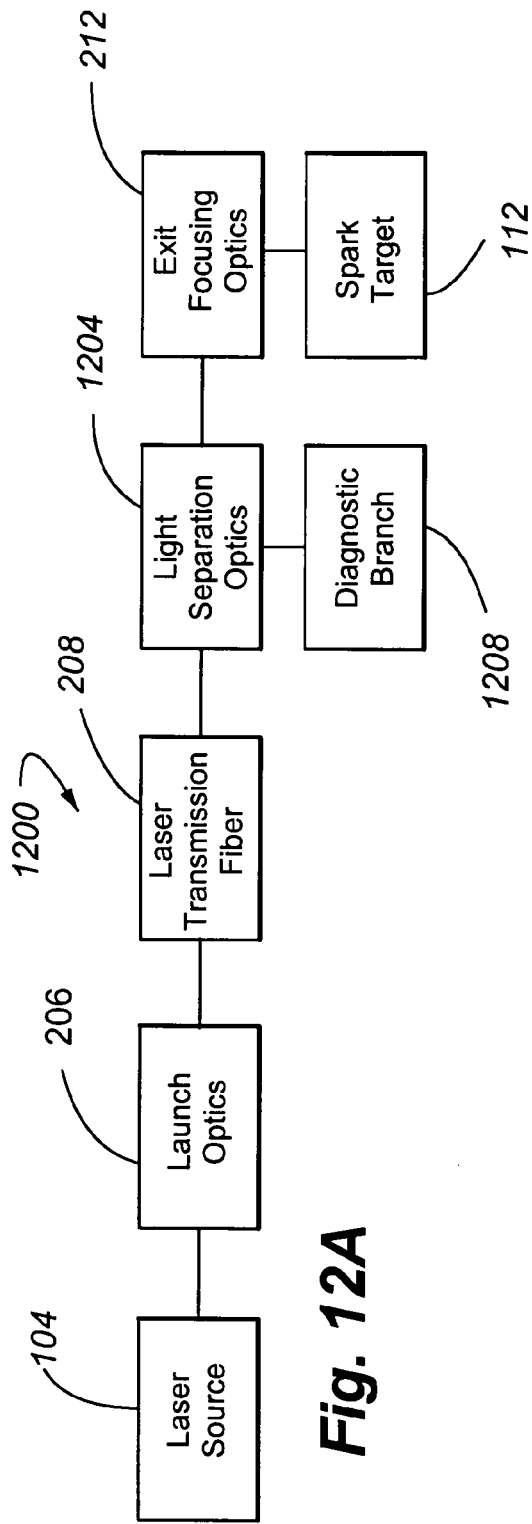
FIG. 12A is a block diagram depicting a spark delivery system in combination with light separation optics and diagnostics in accordance with embodiments of the present invention.

Referring now to FIG. 12A, a block diagram of an embodiment of the present invention incorporating diagnostics is illustrated. For using a diagnostic system in conjunction with the spark generating systems discussed above, FIG. 12A shows a spark and diagnostic system 1200 comprising a laser source 104, launch optics 206, and a laser transmission fiber 208 that ultimately leads to exit focusing optics 212 that are in optical communication with a spark target 112, such as a cylinder of an engine. FIG. 12A further illustrates the use of light separation optics 1204. As discussed further below, the light separation optics 1204 allows at least a portion of the optical pathway leading from the laser source 104 to the spark target 112 to be used as the return path for light collected within the cylinder, such as the light from the spark 608 and/or light from the combustion flame. Light for diagnostic analysis is directed from the light separation optics 1204 to one or more analysis devices of the diagnostic branch 1208.

Figure 12B:
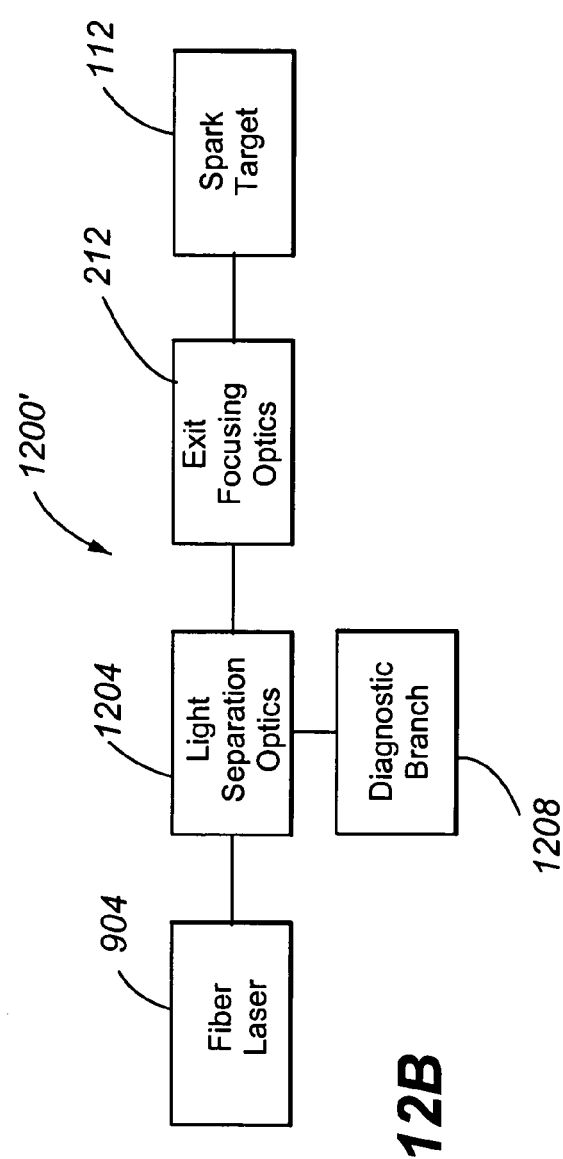
FIG. 12B is a block diagram depicting a spark delivery system in combination with light separation optics and diagnostics for a fiber laser in accordance with embodiments of the present invention.

Referring now to FIG. 12B, and in accordance with embodiments of the present invention, a spark and diagnostic system 1200' is shown that comprises a fiber laser 904 leading to exit focusing optics 212 and spark target 112. In addition, the system 1200' includes, light separation optics 1204 and diagnostic branch 1208.

Figure 13A:
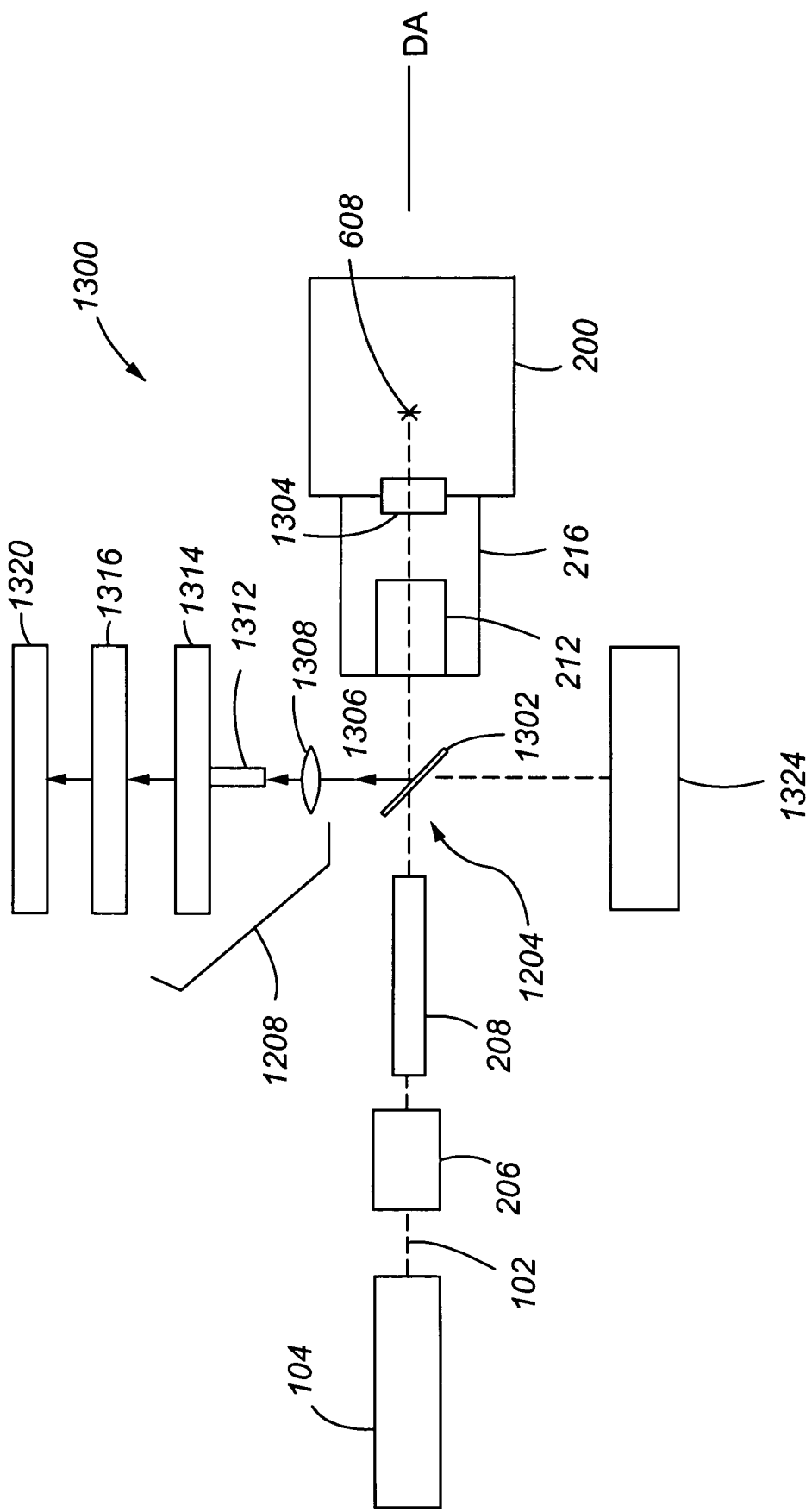
FIG. 13A is a schematic of a spark delivery system in combination with light separation optics and diagnostics in accordance with embodiments of the present invention.

Referring now to FIG. 13A, an illustrated embodiment showing a schematic of a spark generating and optical diagnostic system 1300 is shown. The spark generating and optical diagnostic system 1300 includes a laser source 104, launch focusing optics 206, and laser transmission fiber 208. The laser transmission fiber 208 preferably comprises an optical fiber having a hollow bore, such as the optical fiber shown in FIGS. 4 and 5.

For the spark generating and optical diagnostic system 1300, after passing through the laser transmission fiber 208, the laser light passes through the light separation optics 1204 and encounters the exit focusing optics 212 within the optical spark plug assembly 216. It is to be understood, however, that the location of the light separation optics 1204 may be adjusted from that shown in FIG. 13A. As for example, the light separation optics 1204 could be moved to a location between the exit focusing optics 212 and the window 1304.

In accordance with embodiments of the invention, after passing through the exit focusing optics 212, the laser light preferably passes through a window 1304 leading to the interior of a cylinder of the combustion engine 200, wherein a spark 608 is generated.

The diagnostic light 1306 generated from the spark 608 and/or the light generated from the combustion flame is then collected, such as with the exit focusing optics 212, after it passes through the window 1304. The collected light then encounters the light separation optics 1204 where it is reflected toward the diagnostics branch 1208 that may comprise one or more of the following: focusing optics 1308, optical fiber 1312, dispersive element 1314, photodetector 1316, and other possible diagnostic analysis equipment 1320, including circuitry and a computer. It is to be understood that the above listed components are an example of devices that could be used in a diagnostics branch, and furthermore, it is to be understood that if used, the order of the above listed components may be adjusted. In addition, although not shown, additional optics, such as, but not limited to, lenses and/or mirrors, may be used to focus and/or direct the diagnostic light 1306 as appropriate.

Referring still to FIG. 13A, in accordance with embodiments of the present invention, an optional energy meter 1324 may be provided to measure the laser energy in real time. In FIG. 13A, the optional energy meter 1324 is shown proximate the light separation optics 1204. However, it is to be understood that a beam splitter could be placed at a variety of locations along the laser delivery pathway leading from the laser source 104 to the window 1304. As for example, an optional beam splitter and associated optional energy meter 1324 could be placed between the laser source 104 and launch optics 206, or between the launch optics 206 and the laser transmission fiber 208. Where used, the beam splitter would preferably direct only a small fraction of energy toward an energy meter, thereby allowing measurement of the energy of the laser light directed toward the spark target without withdrawing an excessive amount of laser energy to permit such a measurement.

In accordance with embodiments of the present invention, the light separation optics 1204 may include a dichroic mirror, and more preferably, a "cold mirror" 1302 that is substantially aligned along the optical axis, as shown in FIG. 13A. The cold mirror 1302 preferably has a relatively high transmission for IR light and high reflectivity for visible (and near UV) wavelengths. While one side of the cold mirror 1302 reflects visible light from the engine cylinder for diagnostics, the other side of the cold mirror 1302 can be used as a beam splitter to monitor spark energy. Thus, by way of example and not limitation, for laser spark-delivery using a laser having a wavelength of 1064 nm, the spark-delivery light is transmitted through the cold mirror 1302, while the diagnostic light 1306 is reflected off this axis and passed to a photodetector 1316, such as by way of a suitable lens 1308, an optical fiber 1312, and dispersive element 1314, as shown in FIG. 13A. Additional diagnostic analysis equipment 1320, including circuitry and/or a computer, may be interconnected to the photodetector 1316. It is noted that, for other spark-delivery wavelengths, other wavelength specific optics (e.g., coated mirrors, filters, etc.) could be used. In addition, optics based on polarization splitting are also within the scope of the invention.

Figure 13B:
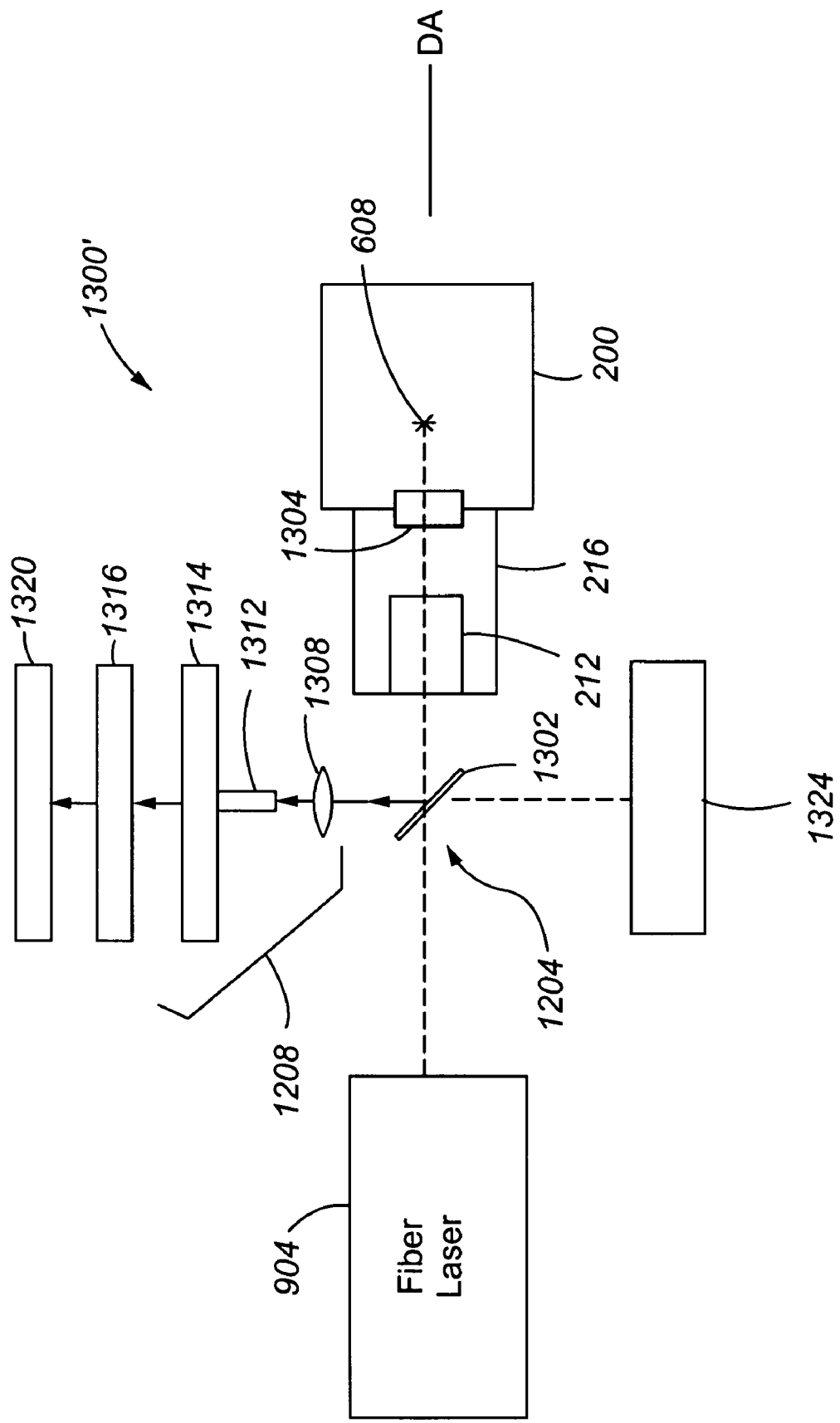
FIG. 13B is a schematic of a spark delivery system using a fiber laser in combination with light separation optics and diagnostics in accordance with embodiments of the present invention.

Referring now to FIG. 13B, an illustrated embodiment that comprises a fiber laser is shown. More particularly, a fiber laser 904 may also be used to generate a spark 608 with subsequent monitoring of the diagnostic light 1306 using various optics and diagnostic equipment. Therefore, for the various embodiments of diagnostic systems described herein, the laser source 104, launch optics 206 and laser transmission fiber 208 may be substituted with a fiber laser 904. As shown in FIG. 13B, the system 1300' may use similar diagnostic components along diagnostic branch 1208 as those components shown in system 1300.

Figure 14:
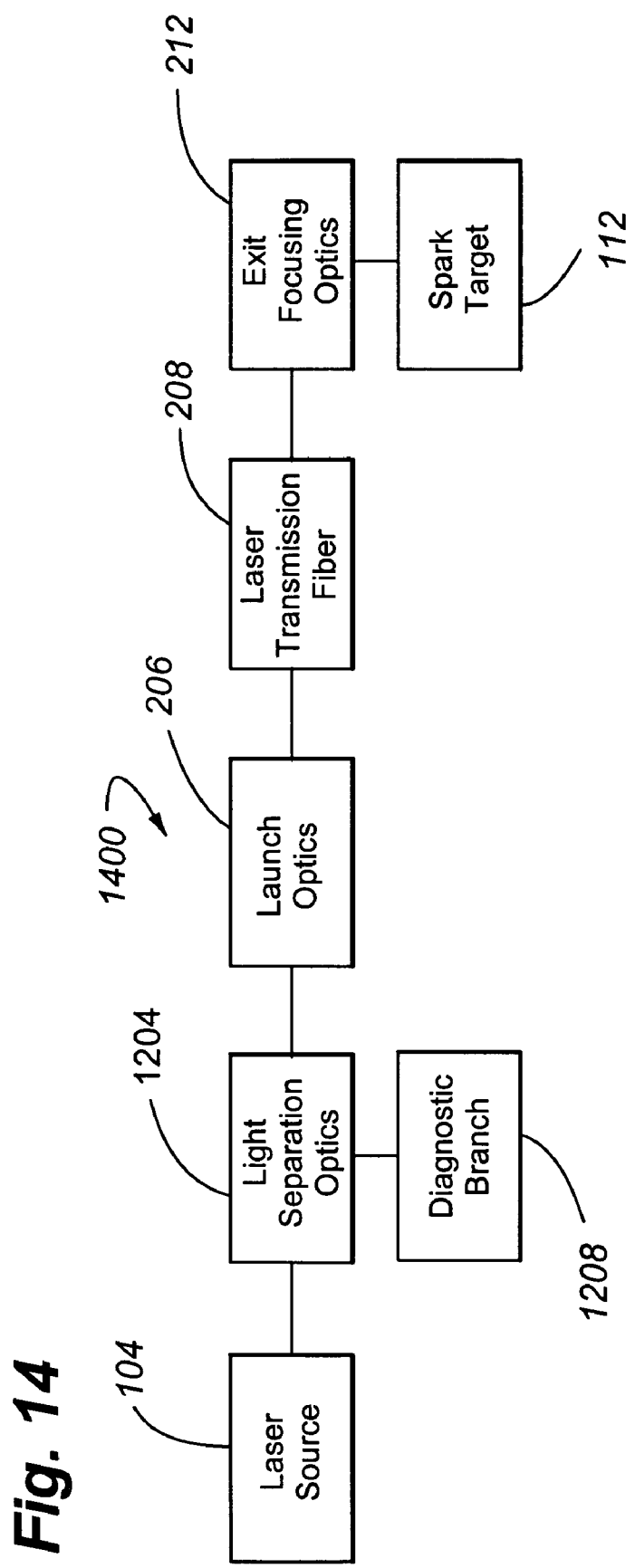
FIG. 14 is a block diagram depicting an alternate spark delivery system in combination with light separation optics and diagnostics in accordance with embodiments of the present invention.

Referring now to FIG. 14, a block diagram of a modified embodiment of the present invention incorporating diagnostics is illustrated. The spark and diagnostic system 1400 shown in FIG. 14 is similar to that shown in FIG. 12A, except the location of the light separation optics 1204 is positioned differently. That is, the light separation optics 1204 is positioned between the laser source 104 and the launch optics 206. Similar to the spark and diagnostic system 1200, system 1400 includes a diagnostic branch 1208 off of the light separation optics 1204. Spark and diagnostic systems 1200 and 1400 illustrate, and those skilled in the art will appreciate, that there are a variety of possible positions for the various components, and alternately configured systems are within the scope of the present invention.

Figure 15:
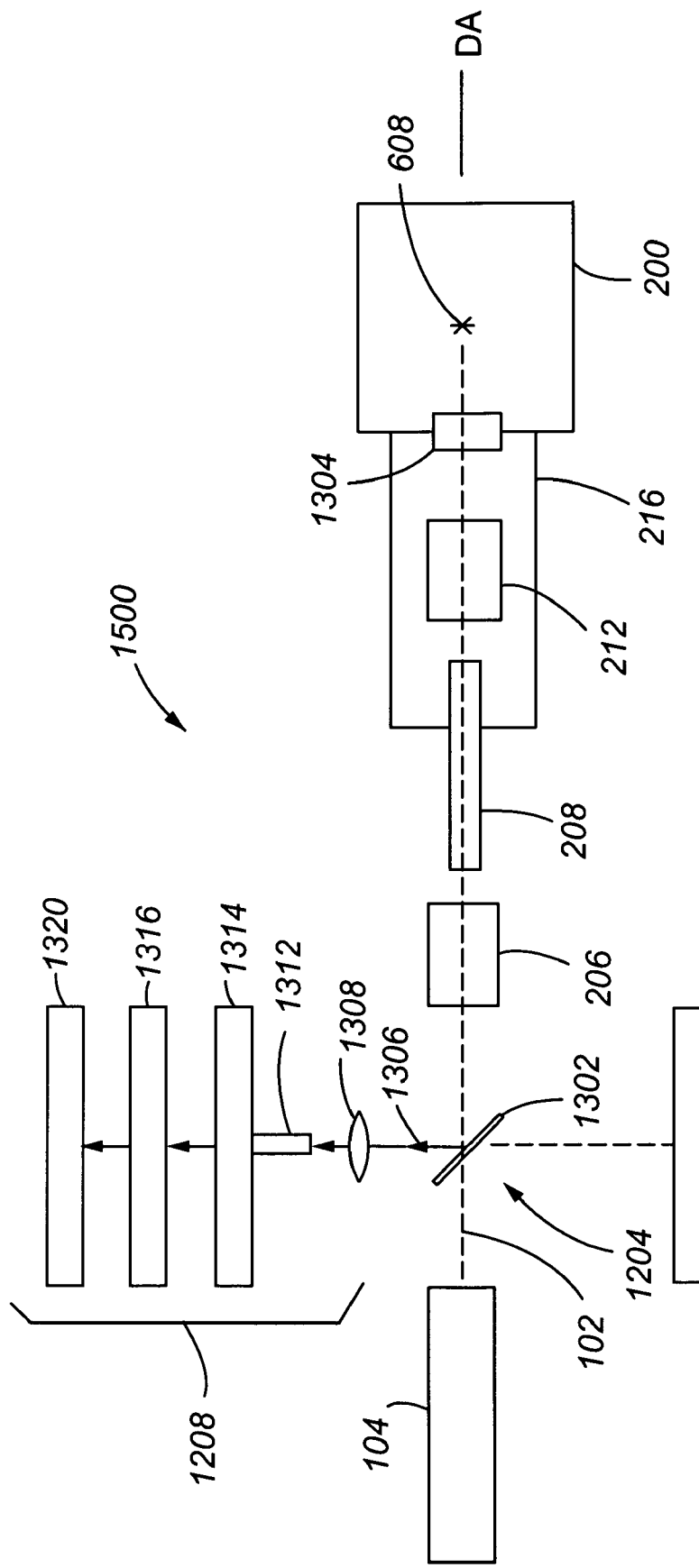
FIG. 15 is an alternate schematic of a spark delivery system in combination with light separation optics and diagnostics in accordance with embodiments of the present invention.

Referring now to FIG. 15, an illustrated embodiment showing an alternate schematic of a spark generating and optical diagnostic system 1500 is shown. The spark generating and optical diagnostic system 1500 includes a laser source 104, launch focusing optics 206, and laser transmission fiber 208. Again, as those skilled in the art will appreciate, it is noted that a fiber laser 904 may be used to generate a spark while also allowing collection of diagnostic light, with the diagnostic branch 1208 positioned in a variety of possible locations.

In contrast to illustrated spark generating and optical diagnostic system 1300 shown in FIG. 13A, light separation optics 1204 shown in FIG. 15 is positioned between the laser source 104 and the launch focusing optics 206. The laser transmission fiber 208 preferably comprises an optical fiber having a hollow bore, such as the optical fiber shown in FIGS. 4 and 5. For the spark generating and optical diagnostic system 1500, after passing through the laser transmission fiber 208, the laser light encounters the exit focusing optics 212 within the optical spark plug 216. In accordance with embodiments of the invention, after passing through the exit focusing optics, the laser light preferably passes through a window 1304 leading to the interior of the cylinder of the combustion engine 200, wherein the spark 608 is generated. The diagnostic light 1306 generated from the spark 608 and/or the light generated from the combustion flame is then collected with the exit focusing optics 212 after it passes through the window 1304. The collected light then encounters the laser transmission fiber 208 where the light is passed through to the launch focusing optics 206, and then becomes incident upon the light separation optics 1204 where the collected diagnostic light 1306 is reflected toward the diagnostics branch 908 that may comprise focusing optics 1308, optical fiber 1312, dispersive element 1314, photodetector 1316, and other diagnostic analysis equipment 1320, including circuitry and/or a computer.

For the schematics discussed above, the diagnostic light 1306 is gathered from the cylinder and is relayed to appropriate optical detectors. As described above, the diagnostic light may be transmitted using an optic fiber, where the optic fiber is the hollow fiber used to transmit the laser light for generating the spark. In accordance with other embodiments of the present invention, the optic fiber may be an additional fiber optic that is either hollow, conventional solid type, or other type. That is, although preferred, the optic fiber transmitting the diagnostic light does not have to be the same as the hollow fiber used to transmit the laser light for generating a spark. In addition, in accordance with yet other embodiments of the present invention, the transmission of the diagnostic light may alternatively be performed in open air without fiber optics, and such transmission may utilize mirrors, lenses, or other optics for such transmission.

Figure 16A:
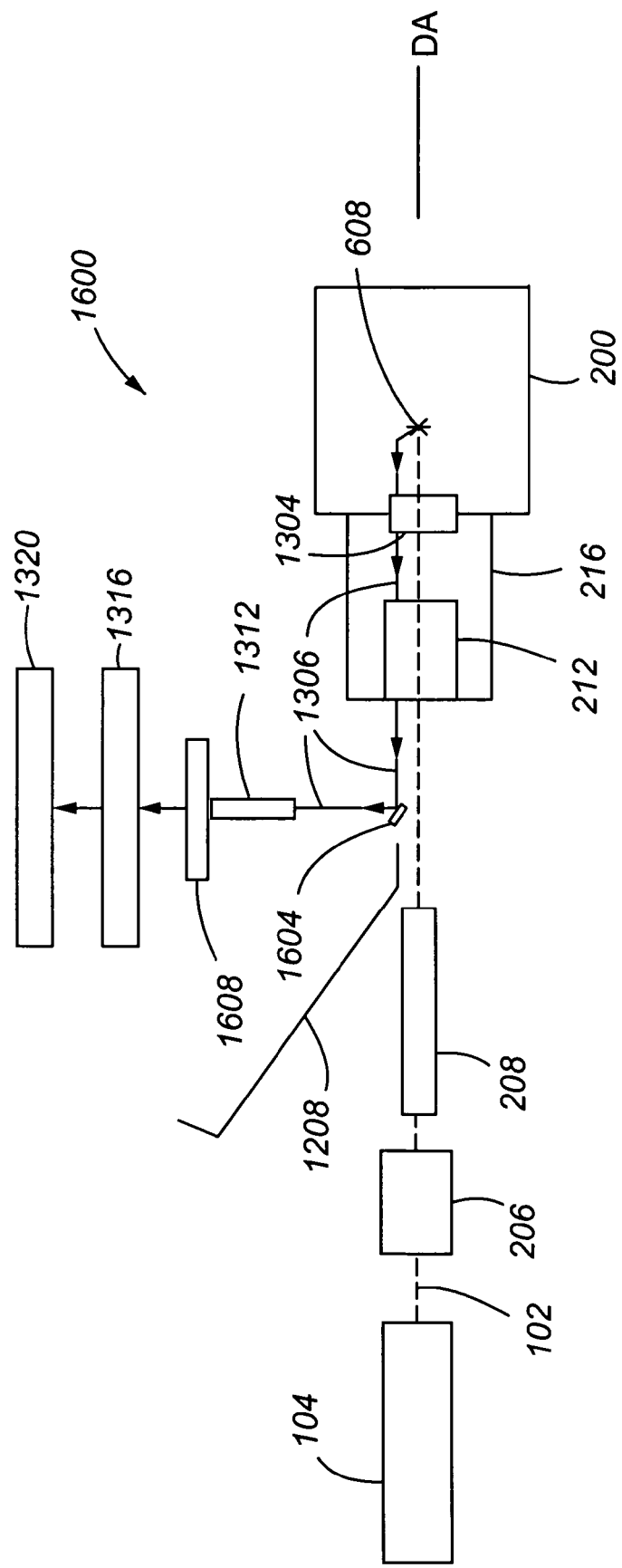
FIG. 16A is an alternate schematic of a spark delivery system in combination with diagnostics in accordance with embodiments of the present invention.

Referring now to FIG. 16A, and consistent with the discussion in the foregoing paragraph, an illustrated embodiment showing an alternate schematic of a spark generating and optical diagnostic system 1600 is shown. The spark generating and optical diagnostic system 1600 includes a laser source 104, launch focusing optics 206, and laser transmission fiber 208. However, in contrast to illustrated spark generating and optical diagnostic systems 1300 and 1500, the diagnostic light 1306 of system 1600 is collected off a different pathway than the delivery axis "DA" of the laser light used to generate spark 608. Various optics may be used to direct the diagnostic light 1306, such as a mirror 1604. As with systems 1300 and 1500, the diagnostics may include a dispersive element. Alternatively, as shown in FIG. 16A, the diagnostics may include a filter 1608, photodetector 1316, and other diagnostic analysis equipment 1320, including circuitry and a computer, such as a spark formation monitor circuit.

Figure 16B:
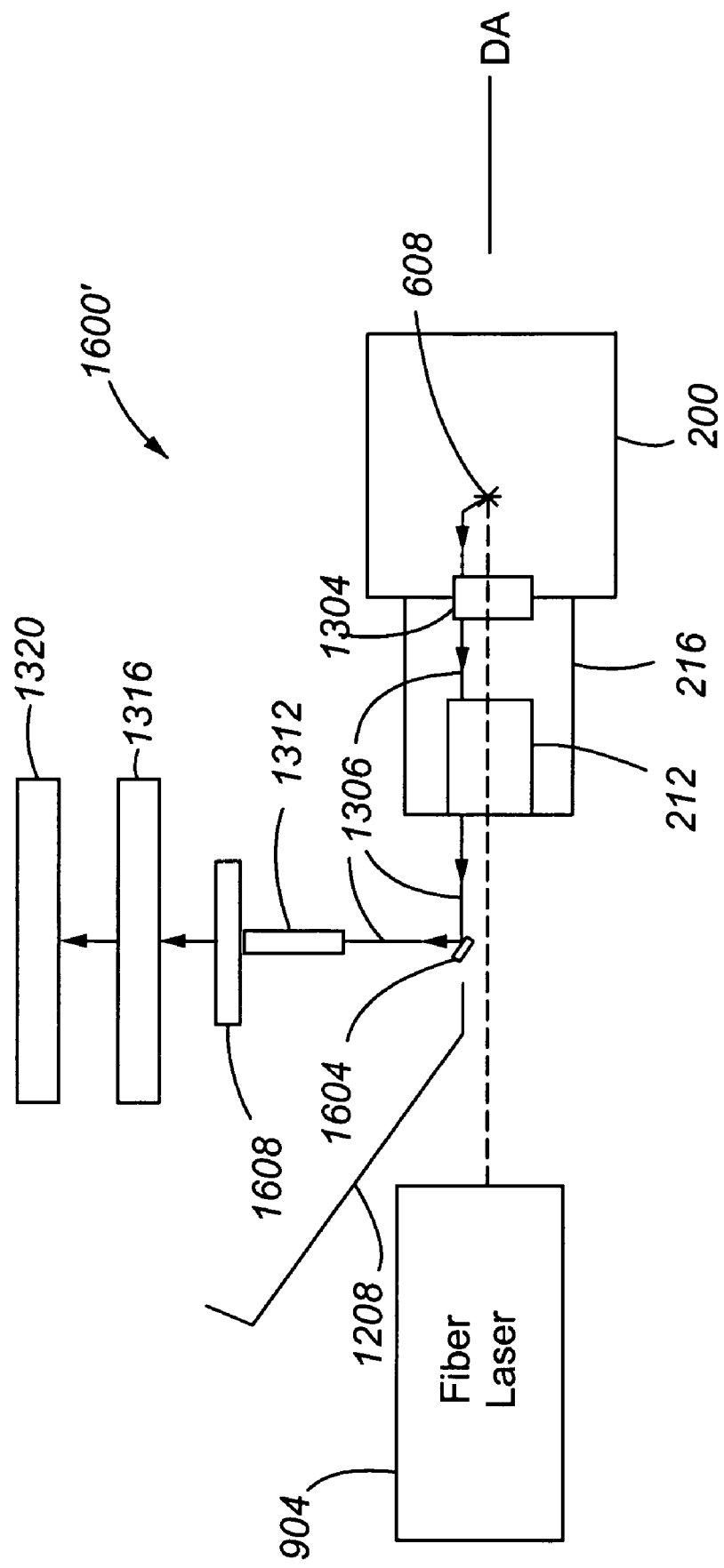
FIG. 16B is an alternate schematic of a spark delivery system using a fiber laser in combination with diagnostics in accordance with embodiments of the present invention.

Referring now to FIG. 16B, an illustrated embodiment showing an alternate schematic of a spark generating and optical diagnostic system 1600' is shown, wherein a fiber laser 904 is utilized. More particularly, FIG. 16B illustrates modification of the embodiment shown in FIG. 16A, wherein a fiber laser 904 is used in place of the laser source 104, launch optics 206 and laser transmission fiber 208.

As noted above, diagnostic light 1306 will typically be gathered from either the spark emission, and/or from emission from the combustion zone or flame. Both sources of light are emitted from within the cylinder. Optical access or optical communication to the inside of the cylinder is preferably provided by the same window 1304 through which the laser light is focused to generate the ignition spark 608. In general, engine operation may "foul" the window 1304, meaning that soot or other particulates may coat the window 1304 causing its optical transmission capacity to decrease. Thus, the window 1304 generally needs to be kept clean. Advantageously, this may be accomplished by passage of the laser energy (fluence) through the window 1304 when generating spark 608. Accordingly, use of the spark generating laser light for this purpose exploits combined spark delivery and diagnostics systems. Alternatively, or in addition to the spark generating laser light, the window 1304 may be kept clean by other means, including heating of the window 1304, thereby causing vaporization of deposited particles. Window heating for cleaning may be via an external heater, or simply due to combustion heat, whereby appropriate design of the material type, thickness, etc., of the window 1304 are addressed. For embodiments using a window cleaning process other than the laser used to generate the spark 608, such a window may be a different window than the window 1304 used to deliver the laser light for generating a spark. That is, one or more cylinders may have a plurality of windows, wherein a first window is used to deliver the a laser light for generating the spark 608, and a second window is used for collection of the diagnostic light 1306.

In an alternative embodiment, since some diagnostic light 1306 will naturally be transmitted out through the window 1304, such light may be relayed to or incident upon a photodetector 1316 without intermediate lenses/optics. Although not illustrated, such a configuration may include a photodiode (or relaying fiber) in close proximity to the window 1304.

For the various embodiments described herein directed to diagnostics, various optics may be used to more efficiently or differently gather, collect, and/or relay the diagnostic light 1306. Such optics may include lenses (simple or complex), curved mirrors, diffractive or active/adaptive optics, or a plurality of the aforementioned. Also, in some cases, this optic may be the same optic used to focus the laser light to form the spark 608. For systems utilizing a diagnostic component of any type, it is again noted that as used herein, both of the terms "optic" and "optics" refer to one or more devices for altering a beam of light, as for example, a single lens (simple or compound), a mirror (including a curved mirror), an active or adaptive optic, a diffractive optic, or a plurality of the aforementioned components.

In accordance with embodiments of the present invention, the window 1304 may comprise the entirety of the exit focusing optics 212, or the window 1304 may comprise an element of the exit focusing optics 212, such that the window 1304 aids in formation of the spark 608. Furthermore, for embodiments utilizing a fiber laser 904, the integral focusing lens 1104 may comprise the window 1304.

For embodiments of the present invention directed to diagnostics, light separation optics 1204 and/or the diagnostic branch 1208 preferably comprise devices for manipulating and/or detecting the diagnostic light 1306. As described above and shown in the figures, such devices include one or more dispersive elements 1314, and/or photodetectors 1316, as may be appropriate. The diagnostic light 1306 is measured to infer various spark and combustion parameters. Some measurements, such as confirmation of spark delivery and/or confirmation of ignition, can be based on optical intensity (or power or energy) versus time, and such measurements can be achieved with many types of photodetectors, where a "photodetector" as defined herein means of at least one of many types of available transducers that can measure optical intensity by conversion to an electrical or other type of signal. Examples of common photodetectors include: photodiode, phototransistor, avalanche photodiode, photomultiplier tube, CMOS, CCD array, or intensified CCD, etc.

For diagnostic light detection directed to the presence of light and not the spectra of the light, a photodetector is suitable. In other cases where the spectral content of the diagnostic light is of interest, the diagnostic light must be passed to a dispersive element 1314 prior to being measured with a photodetector 1316. A dispersive element, based usually on refraction or diffraction, can be used to spatially separate light of different wavelengths. Examples of dispersive elements include, but are not necessarily limited to prisms, diffraction gratings, monochromators, spectrometers, and optical multichannel analyzers (OMAs). In addition, optical band-pass filters (also known as notch-transmission filters) could also be adapted for this purpose. As used herein, a dispersive element can be any of the elements listed above as may be appropriate for the given application. It is noted that some dispersive elements include within them a photodetector, but if not, then the output of the dispersive element is preferably measured with a photodetector. These dispersive elements can, in general, be placed anywhere in the optical train of the diagnostic light 1306, as long as they are between the source of diagnostic light 1306 and the photodetector 1316. For example, a dispersive element comprising a band-pass filter could be used on either side of the collection optic fiber, but would need a photodetector at the output end of the collection optic fiber.

Figure 17:
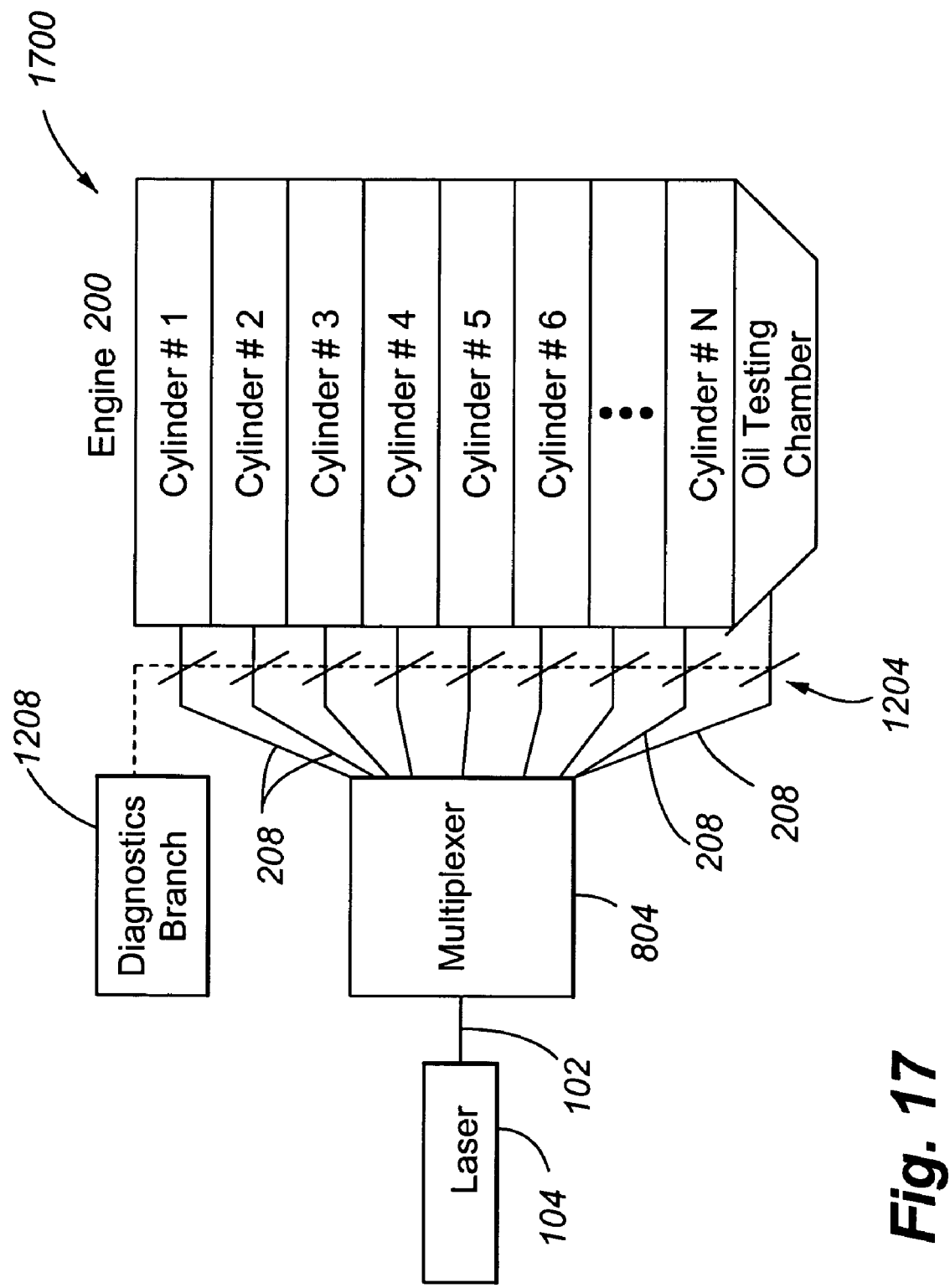
FIG. 17 is a block diagram/schematic of a spark delivery system using a multiplexer, in combination with diagnostics in accordance with embodiments of the present invention.

Referring now to FIG. 17, a further illustrated embodiment of a spark generating and diagnostic system 1700 is shown. The spark generating and optical diagnostic system 1700 generally includes the components discussed above for system 800 that incorporates a multiplexer, and further includes a diagnostic branch 1208 for analysis of the diagnostic light from the various engine cylinders. Although light separation optics 1204 are shown between the cylinders and the laser transmission fibers 208, it is to be understood that the light separation optics could be located in a different location, such as those positions described above. Furthermore, although only one diagnostic branch 1208 is shown, a plurality of diagnostics branches could be used. Such a configuration would be less efficient than that shown in FIG. 17, but mention is made of such a possible embodiment to further emphasize the variety of configurations possible for the different components of the systems described herein. Furthermore, as those skilled in the art will appreciate, a diode pump with multiplexed fiber lasers may be utilized to provide optical spark plugs with laser light, and such an configuration can include diagnostics similar to that shown in the figures and described above. Finally, the multiplexing may provide a laser beam for generating a spark to an oil testing chamber of the engine for analysis of oil. A description of such a feature is discussed below. It is also noted that, although not shown, other engine or vehicle fluids could also be tested, including coolants, brake fluid, etc.

In accordance with embodiments of the present invention, a method of performing diagnostics is also provided. The method comprises providing a beam of laser light using a laser generator and conveyance apparatus. The laser generator and conveyance apparatus may comprise at least one of either: (a) a hollow optic fiber, or (b) a fiber laser. The method further includes focusing the laser light to generate a spark, and receiving a diagnostic light from at least the spark and a flame resulting from the spark. In accordance with embodiments of the present invention, the spark may be generated within at least a portion of an engine so that diagnostics are performed on light emitted from within a portion of the engine, such as within a cylinder of the engine. The method may also include multiplexing the laser light to a plurality of spark targets, as for example, a number of cylinders. In addition, the method may comprise providing a photodetector for receiving of the diagnostic light, and further comprise providing a dispersive element for separating at least one wavelength of the diagnostic light prior to receiving the diagnostic light, such as on a photodetector.

The following paragraphs discuss some of the possible diagnostic schemes for use with embodiments of the present invention. It is to be understood that other approaches, refinements, and/or modifications of the diagnostics listed below or otherwise described herein are within the scope of the present invention.

By collecting light during the time interval in which the spark is expected, and by monitoring the spark's intensity (or power or energy), spark formation can be monitored. As for example, the presence of a light signal above some threshold intensity during that time period would correspond to successful spark formation. Note that although not required, a dispersive element could be used even if only verification of spark formation is being sought from the diagnostic light. With regard to spark formation, as those skilled in the art will appreciate, embodiments of the diagnostic systems described herein are anticipated to allow for cycle-to-cycle control schemes.

Spark emission from various atomic lines has been used for both spark temperature measurements and fuel-to-air measurements. See Phuoc, et al., 2001, "Optical Characterization of the Laser-induced Spark In Air," Optical Diagnostics in Engineering, 5, pp. 13-26, the content of which is incorporated herein by reference in its entirety. In general, spark formation causes molecules in the spark volume to dissociate into atoms. Some of those atoms are excited to elevated energy levels, and then emit light at discrete wavelengths (frequencies) yielding spectral lines at locations corresponding to the atomic energy level differences. Measuring the light emitted from species created within the spark is generally termed Laser Induced Breakdown Spectroscopy (LIBS).

One approach to spark temperature measurement uses emission lines from atomic oxygen at 748.07 nm and 777.54 nm, and can provide a spark temperature measurement if one assumes that the plasma is in thermal equilibrium with a Boltzmann distribution. (Other line systems also are possible.) The spark temperature is useful for characterization of the spark itself, and may allow inference of other information associated with: the ignition event, the subsequent combustion event, and/or pollutant formation in the subsequent combustion event.

Light emission from the spark also can be used to obtain real time measurement of the local fuel-to-air ratio. Again, a LIBS setup is used, though different atomic lines are employed. For example, is has been shown that a laser spark created in $CH_4$ emits a strong $H_\alpha$ line at 656.3 nm due to excited hydrogen dissociated from the methane fuel. See Phuoc, et al., 2002, "Laser-induced Spark for Measurements of the Fuel-to-Air Ratio of a Combustible Mixture," FUEL, 81, pp. 1761-1765, the contents of which are incorporated herein by reference in its entirety. The ratio of this hydrogen line to the oxygen triplet at 777.54 nm can be correlated with the equivalence ratio. Ratios of optical emission lines from C/N, CN/air, C/O can also be used for local equivalence ratios, while CH/OH, $C_2$/OH signal ratios from post spark combustion can be used for overall equivalence ratio. See Ferioli, et al., 2003, "Laser-Induced Breakdown Spectroscopy for On-Line Engine Equivalence Ratio Measurements," Applied Spectroscopy, 57, pp. 1183-1189; and Morrell, et al., 2001, "Interpretation of Optical Emissions for Sensors in Liquid Fueled Combustors", AIAA 2001-0787; the contents of the foregoing references are incorporated herein by reference in their entirety. The local fuel-to-air ratio is useful for combustion monitoring and may also provide information on global fuel-to-air, and subsequent combustion.

As noted above, the diagnostic setup can also be used to collect combustion emission light; that is, light emitted from species within the flame, as opposed to spark. Such diagnostics are termed Optical Emission Spectroscopy (OES). Spectral information on the strengths of various atomic lines, or molecular bands, can be used to infer temperature. For example, a Boltzmann analysis of rotational lines within the OH band at ~308 nm can be used to measure temperature. Similar measurements using other systems (e.g., NH or N2) are also possible.

The OES can also be used to study the presence of certain pollutant species, as for example formaldehyde, by measuring the light signal at wavelengths associated with the given species of interest. Such measurements may be useful for combustion and atmospheric monitoring to understand basic combustion processes, and to verify combustion models.

In the same way that pollutant species can be monitored, light from "combustion intermediates" can be used to measure the presence of combustion intermediates. Combustion intermediates are species that are created/destroyed during the combustion process. Such measurements may be useful to understand basic combustion processes, and to verify combustion models. In addition, measurements may be useful for potentially understanding pollutant formation, characterization of combustion performance, and/or for feedback pertaining to cycle control, as for example, adjusting timing and/or pressure, etc., to improve engine performance.

Monitoring the presence of certain species, such as formaldehyde, is also anticipated to provide a means of monitoring/avoiding knock. In general, knock is auto-ignition of unburned gases in the engine, and is generally detrimental to engine operation.

During operation, buildup can occur on the surfaces of pistons, combustion chambers, and gas turbine blades. LIBS can be utilized to monitor this buildup, if the ignition spark (or another spark added for this purpose) is incident on the piston head (or chamber wall or other targeted area). As for example, for a piston a laser spark on a clean piston would show only lines corresponding to aluminum or steel, depending on the piston construction. Once buildup occurs, LIBS will indicate the presence of carbon and other ash compounds, such as cadmium, phosphorus, sulfur, etc. Likewise, the spark off of a turbine blade would show only the composition of the blade (typically steel). Again, once buildup occurs, LIBS will indicate the presence of carbon and other ash compounds (cadmium, phosphorus, sulfur, etc).

Combustion temperature monitoring using LIBS is also available. The temperature can be determined by measuring at a distance the time of flight from the breakdown until the receipt of sound signal. The speed of sound in a gas is directly related to the temperature of a gas. Thus, the delay between sparking and receipt of sound in a hot gas will be shorter than a cooler gas. The receptor for this system could be a microphone, or simply a relatively simple piezoelectric sensor, similar to the NOx sensor in an automobile. High temperature microphones are quite expensive, but the fidelity required for this application is very low, so a much simpler microphone and/or accelerometer based system could also suffice.

The information attainable from the above diagnostics, and the potential for control, may be significantly enhanced if the optical diagnostics are correlated or used in connection with other diagnostics. These other diagnostics include standard combustion techniques such as: pressure sensing, temperature sensing, exhaust emissions analysis, and ion-sensing.

In accordance with embodiments of the present invention, an additional optional application of laser ignition may be for sensing contaminant build up in engine oil and/or other fluids (coolant, transmission fluid, hydraulic oil). As noted, LIBS is an analytical tool used to detect the presence of elements. Accordingly, the present invention may be adapted for generating a spark on the surface of an oil sample. Such a spark will produce light in the carbon and hydrogen bands as expected. However, metals in the oil may also be detected because the meals will emit light at specific frequency bands. Although LIBS is one of the techniques sometimes used to characterize oils, it has previously been used as an offline process. In general, it would be relatively expensive to install a LIBS system on an engine to continuously monitor oil quality. However, for embodiments of the present invention where the laser ignition system is already in use to generate sparks for combustion, then it is relatively easy to add the functionality to add an additional fiber into an oil/fluid test chamber to monitor the oil/fluid on a continuous or periodic basis. Such monitoring system of LIBS to monitor oil and fluid quality has application to reciprocating items, as well as gas turbines.

In summary, for certain embodiments of the present invention, the combined spark generating and diagnostic systems described herein include the following advantages: (a) the high intensity laser beam used for ignition provides a way to keep the window clean because in the absence of the ignition laser it would more quickly become opaque; (b) the hollow fiber used to deliver high power laser for the spark igniting the fuel/air mixture also provides a means to transmit the combustion diagnostic light from the cylinder to the detector; and (c) the ignition spark directly provides the chance to perform optical diagnostics based on the spark emission light via laser induced breakdown spectroscopy.

While various embodiments of the present invention have been described in detail, it is apparent that modifications and adaptations of those embodiments will occur to those skilled in the art. However, it is to be expressly understood that such modifications and adaptations are within the spirit and scope of the present invention.

The present invention, in various embodiments, includes components, methods, processes, systems and/or apparatus substantially as depicted and described herein, including various embodiments, subcombinations, and subsets thereof. Those of skill in the art will understand how to make and use the present invention after understanding the present disclosure. The present invention, in various embodiments, includes providing devices and processes in the absence of items not depicted and/or described herein or in various embodiments hereof, including in the absence of such items as may have been used in previous devices or processes, e.g., for improving performance, achieving ease and\or reducing cost of implementation.

The foregoing discussion of the invention has been presented for purposes of illustration and description. The foregoing is not intended to limit the invention to the form or forms disclosed herein. In the foregoing Detailed Description for example, various features of the invention are grouped together in one or more embodiments for the purpose of streamlining the disclosure. This method of disclosure is not to be interpreted as reflecting an intention that the claimed invention requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the invention.

Moreover though the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A spark and diagnostic system for an engine, the system comprising:
   a laser light source for generating a laser beam;
   launch optics for focusing said laser beam;
   a laser transmission fiber for receiving said laser beam from said launch optics and transmitting said laser beam;
   exit focusing optics for receiving said laser beam from said laser transmission fiber and focusing said laser beam for generating a spark in a fuel and air mixture within the engine;
   wherein said laser transmission fiber transmits diagnostic light generated from at least one of said spark or from a flame from combustion of the fuel and air mixture;
   a diagnostic apparatus for analyzing said diagnostic light from said laser transmission fiber; and
   a dichroic mirror located between said exit focusing optics and said diagnostic apparatus, wherein at least a portion of said laser beam passes through said dichroic mirror before generating said spark in the engine, and wherein at least a portion of the diagnostic light is reflected off said dichroic mirror and conveyed to said diagnostic apparatus.

2. The system as claimed in claim 1, wherein said laser transmission fiber comprises a hollow bore and a wall surrounding said hollow bore, wherein the wall comprises an inside surface that comprises at least one of an interior layer and an interior coating.

3. The system as claimed in claim 1, further comprising a window allowing optical communication of the diagnostic light to the laser transmission fiber.

4. The system as claimed in claim 1, further comprising a multiplexer located between said laser light source and said exit focusing optics.

5. The system as claimed in claim 1, wherein said dichroic mirror comprises a cold mirror.

6. The system as claimed in claim 1, further comprising at least one of a dispersive element or a band-pass filter between said dichroic mirror and said diagnostic apparatus.

7. The system as claimed in claim 1, wherein said diagnostic apparatus is selected from the group consisting of a circuit and a computer.

8. The system as claimed in claim 1, wherein at least one of said launch optics and said exit focusing optics comprises at least one lens.

9. The system as claimed in claim 1, wherein at least one of said launch optics and said exit focusing optics comprises at least one curved mirror.

10. The system as claimed in claim 1, wherein at least one of said launch optics and said exit focusing optics are selected from the group consisting of diffractive optics, adaptive optics, and a combination thereof.

11. A diagnostic system for an engine, the engine including a cylinder for containing a fuel and air mixture to be ignited, the system comprising:
    a means for generating a laser beam;
    a fiber optic means for conveying said laser beam, the fiber optic means comprising a hollow bore and a wall surrounding said hollow bore, wherein the wall comprises an inside surface that comprises at least one of an interior layer and an interior coating;
    a means for focusing the laser beam to generate a spark and ignite the fuel and air mixture within the cylinder;
    a means for transmitting diagnostic light from the cylinder, the diagnostic light comprising light from at least one of said spark or a flame from combustion of the fuel and air mixture; and
    a means for performing diagnostic analysis of said diagnostic light.

12. The system as claimed in claim 11, further comprising a means for transmitting and reflecting, wherein said means for transmitting and reflecting transmits said laser beam and reflects said diagnostic light.

13. The system as claimed in claim 12, wherein said laser beam and said diagnostic light from said cylinder traverse a substantially common path between said means for transmitting and reflecting and the cylinder.

14. The system as claimed in claim 12, further comprising an optical fiber between said means for transmitting and reflecting and said means for performing diagnostic analysis, wherein said optical fiber conveys at least a portion of said diagnostic light.

15. The system as claimed in claim 11, wherein said means for performing diagnostic analysis comprises a photodetector.

16. A spark and diagnostic system, comprising:
    a means for generating a beam of laser light, wherein said means for generating a beam of laser light is selected from the group consisting of:
    (a) a laser source, launch optics, and hollow optic fiber; and
    (b) a fiber laser;
    a means for focusing the laser light to generate a spark, wherein said means for focusing the laser light is selected from the group consisting of diffractive optics, active optics, adaptive optics, and a combination thereof; and
    a photodetector means for receiving diagnostic light from at least one of the spark or a flame resulting from the spark.

17. The system as claimed in claim 16, further comprising a means for separating the wavelengths of said diagnostic light.

18. The system as claimed in claim 17, wherein said means for separating comprises at least one device selected from the group consisting of a prism, a diffraction grating, a monochromator, a spectrometer, an optical multi-channel analyzer, and an optical band-pass filter.

19. The system as claimed in claim 16, wherein said photodetector means for receiving comprises at least one device selected from the group consisting of a photodiode, a phototransistor, an avalanche photodiode, a photomultiplier tube, a complementary metal oxide semiconductor, a charge-coupled device, an intensified charge-coupled device, and a contact image sensor.

20. The system as claimed in claim 16, wherein said means for focusing the laser light is in optical communication with an engine cylinder.

21. The system as claimed in claim 16, wherein a diagnostics performed by the system comprises at least one of a spark formation, an optical intensity, a LIBS, an element analysis, a pollutant analysis, an OES, a cycle measurement, a temperature analysis, a pressure sensing, an exhaust emissions analysis, an ion-sensing, a knock indicator, a buildup analysis, and a contaminant monitoring.

22. The system as claimed in claim 16, further comprising a multiplexer located between said means for generating and said means for focusing.

23. A method of generating a spark and collecting a diagnostic light, the method comprising:

providing a beam of laser light using a laser generator and conveyance apparatus, the laser generator and conveyance apparatus comprising at least one of either;
(a) a hollow optic fiber comprising a hollow bore and a wall surrounding said hollow bore, wherein the wall comprises an inside surface that comprises at least one of an interior layer and an interior coating; or
(b) a fiber laser;
focusing the laser light to generate a spark in a fuel and air mixture; and
receiving a diagnostic light from at least one of the spark or a flame resulting from combustion of the fuel and air mixture.

24. The method as claimed in claim 23, further comprising substantially cleaning a window proximate a location of the fuel and air mixture.

25. The method as claimed in claim 23, further comprising multiplexing the laser light to a plurality of spark targets.

26. The method as claimed in claim 23, further comprising providing a photodetector for said receiving of the diagnostic light.

27. The method as claimed in claim 26, further comprising providing a dispersive element for separating a wavelength of the diagnostic light prior to said receiving the diagnostic light.

28. A spark and diagnostic system for an engine, the system comprising:
a laser light source for generating a laser beam;
launch optics for focusing said laser beam;
a laser transmission fiber for receiving said laser beam from said launch optics and transmitting said laser beam; and
exit focusing optics for receiving said laser beam from said laser transmission fiber and focusing said laser beam for generating a spark in a fuel and air mixture within the engine;
wherein at least one of said launch optics and said exit focusing optics are selected from the group consisting of diffractive optics, adaptive optics, and a combination thereof; and
wherein said laser transmission fiber transmits diagnostic light generated from at least one of said spark or from a flame from combustion of the fuel and air mixture.

29. The system as claimed in claim 28, wherein said laser transmission fiber comprises hollow bore and a wall surrounding said hollow bore, wherein the wall comprises an inside surface that comprises at least one of an interior layer and an interior coating.

30. The system as claimed in claim 28, wherein said laser transmission fiber comprises a fiber laser.

31. The system as claimed in claim 28, further comprising a window allowing optical communication of the diagnostic light to the laser transmission fiber.

32. The system as claimed in claim 28, further comprising a multiplexer located between said laser light source and said exit focusing optics.

33. The system as claimed in claim 28, further comprising a diagnostic apparatus for analyzing said diagnostic light from said laser transmission fiber.

34. The system as claimed in claim 33, further comprising a dichroic mirror located between said exit focusing optics and said diagnostic apparatus, wherein at least a portion of said laser beam passes through said dichroic mirror before generating said spark in the engine, and wherein at least a portion of the diagnostic light is reflected off said dichroic mirror and conveyed to said diagnostic apparatus.

35. A spark and diagnostic system for an engine, the system comprising:
a laser light source for generating a laser beam;
launch optics for focusing said laser beam;
a laser transmission fiber for receiving said laser beam from said launch optics and transmitting said laser beam, said laser transmission fiber comprising a hollow bore and a wall surrounding said hollow bore, wherein the wall comprises an inside surface that comprises at least one of an interior layer and an interior coating; and
exit focusing optics for receiving said laser beam from said laser transmission fiber and focusing said laser beam for generating a spark in a fuel and air mixture within the engine;
wherein diagnostic light generated from at least one of said spark or from a flame from combustion of the fuel and air mixture passes to a diagnostic apparatus for analyzing said diagnostic light.

36. The system as claimed in claim 35, further comprising a multiplexer located between said laser light source and said exit focusing optics.

37. The system as claimed in claim 35, further comprising light separation optics located between said exit focusing optics and said diagnostic apparatus, wherein at least a portion of said laser beam passes through said light separation optics before generating said spark in the engine, and wherein at least a portion of the diagnostic light is reflected off said light separation optics and conveyed to said diagnostic apparatus.

38. The system as claimed in claim 37, wherein the light separation optics comprises a dichroic mirror located downstream of the laser transmission fiber.

39. The system as claimed in claim 38, wherein said dichroic mirror comprises a cold mirror.

40. The system as claimed in claim 38, further comprising at least one of a dispersive element or a band-pass filter between said dichroic mirror and said diagnostic apparatus.

41. The system as claimed in claim 35, wherein said diagnostic apparatus is selected from the group consisting of a circuit and a computer.

42. The system as claimed in claim 35, wherein at least one of said launch optics and said exit focusing optics are selected from the group consisting of diffractive optics, adaptive optics, and a combination thereof.

43. A method of generating a spark and collecting a diagnostic light, the method comprising:
providing a beam of laser light using a laser generator and conveyance apparatus, the laser generator and conveyance apparatus comprising a fiber laser;
focusing the laser light to generate a spark in a fuel and air mixture; and
receiving a diagnostic light from at least one of the spark or a flame resulting from combustion of the fuel and air mixture, said receiving including separating a wavelength of the diagnostic light using a dispersive element.

44. The method as claimed in claim 43, further comprising using a photodetector for said receiving of the wavelength of the diagnostic light, wherein said photodetector comprises at least one device selected from the group consisting of a photodiode, a phototransistor, an avalanche photodiode, a photomultiplier tube, a complementary metal oxide semiconductor, a charge-coupled device, an intensified charge-coupled device, and a contact image sensor.

45. The method as claimed in claim 43, further comprising multiplexing the laser light to a plurality of spark targets.

46. A diagnostic system for an engine, the engine including a cylinder for containing a fuel and air mixture to be ignited, the system comprising:
- a means for generating a laser beam;
- a fiber optic means for conveying said laser beam, the fiber optic means comprising a fiber laser;
- a means for focusing the laser beam to generate a spark and ignite the fuel and air mixture within the cylinder;
- a means for transmitting diagnostic light from the cylinder, the diagnostic light comprising light from at least one of said spark or a flame from combustion of the fuel and air mixture; and
- a means for performing diagnostic analysis of said diagnostic light.

47. The diagnostic system as claimed in claim 46, further comprising a means for multiplexing in optical communication with the means for generating.

48. The system as claimed in claim 46, further comprising a means for transmitting and reflecting, wherein said means for transmitting and reflecting allows passage of said laser beam and reflects said diagnostic light.

49. The system as claimed in claim 48, wherein the means for transmitting and reflecting comprises a mirror.

50. The system as claimed in claim 12, wherein the means for transmitting and reflecting comprises a mirror.

51. The system as claimed in claim 1, wherein the laser transmission fiber comprises a fiber laser.

* * * * *